(12) United States Patent
Bost et al.

(10) Patent No.: US 8,865,405 B2
(45) Date of Patent: *Oct. 21, 2014

(54) COMPOSITIONS AND METHODS OF SELECTIVE NUCLEIC ACID ISOLATION

(71) Applicant: Applied Biosystems, LLC, Carlsbad, CA (US)

(72) Inventors: Douglas Bost, Foster City, CA (US); Lawrence Greenfield, Santa Clara, CA (US)

(73) Assignee: Applied BioSystems LLC, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/959,725

(22) Filed: Aug. 5, 2013

(65) Prior Publication Data

US 2014/0065626 A1 Mar. 6, 2014

Related U.S. Application Data

(60) Continuation of application No. 12/471,292, filed on May 22, 2009, now Pat. No. 8,507,198, which is a division of application No. 11/789,352, filed on Apr. 23, 2007, now Pat. No. 7,537,898, which is a division of application No. 10/306,347, filed on Nov. 27, 2002, now Pat. No. 7,208,271.

(60) Provisional application No. 60/334,029, filed on Nov. 28, 2001.

(51) Int. Cl.
| C12Q 1/68 | (2006.01) |
| C07H 21/00 | (2006.01) |
| C07H 21/02 | (2006.01) |
| C07H 21/04 | (2006.01) |
| C12N 15/10 | (2006.01) |

(52) U.S. Cl.
CPC .......... *C12N 15/101* (2013.01); *C12N 15/1006* (2013.01); *C12Q 1/6806* (2013.01)
USPC ......... 435/6.1; 536/22.1; 536/23.1; 536/24.3; 536/25.4

(58) Field of Classification Search
CPC ......... C12Q 1/68; C12Q 1/6806; C12N 15/10
USPC ................ 435/6.1; 536/22.1, 23.1, 24.3, 25.4
See application file for complete search history.

(56) References Cited

U.S. PATENT DOCUMENTS

| 4,340,674 A | 7/1982 | Manis et al. |
| 4,420,517 A | 12/1983 | Ali |
| 4,483,920 A | 11/1984 | Gillespie et al. |
| 4,623,723 A | 11/1986 | Keller et al. |
| 4,648,975 A | 3/1987 | Barkatt et al. |
| 4,843,155 A | 6/1989 | Chomczynski |
| 4,895,714 A | 1/1990 | Faulk |
| 4,900,677 A | 2/1990 | Hewitt |
| 4,923,978 A | 5/1990 | McCormick |
| 5,075,430 A | 12/1991 | Little et al. |
| 5,106,966 A | 4/1992 | Thomas et al. |
| 5,137,816 A | 8/1992 | Rolfe et al. |
| 5,155,018 A | 10/1992 | Gillespie et al. |
| 5,175,271 A | 12/1992 | Thomas et al. |
| 5,234,809 A | 8/1993 | Boom et al. |
| 5,329,000 A | 7/1994 | Woodard et al. |
| 5,342,931 A | 8/1994 | Woodward et al. |
| 5,346,994 A | 9/1994 | Chomczynski |
| 5,405,951 A | 4/1995 | Woodard |
| 5,438,127 A | 8/1995 | Woodard et al. |
| 5,438,129 A | 8/1995 | Woodard et al. |
| 5,503,816 A | 4/1996 | Woodard et al. |
| 5,523,392 A | 6/1996 | Woodard et al. |
| 5,525,319 A | 6/1996 | Woodard et al. |
| 5,534,054 A | 7/1996 | Woodard et al. |
| 5,576,196 A | 11/1996 | Horn et al. |
| 5,606,046 A | 2/1997 | Woodard et al. |
| 5,610,290 A | 3/1997 | Woodard et al. |
| 5,610,291 A | 3/1997 | Woodard et al. |
| 5,616,701 A | 4/1997 | Woodard et al. |
| 5,625,054 A | 4/1997 | Woodard et al. |
| 5,637,687 A | 6/1997 | Wiggins |
| 5,641,665 A | 6/1997 | Hobart et al. |
| 5,650,506 A | 7/1997 | Woodard et al. |
| 5,658,548 A | 8/1997 | Padhye et al. |
| 5,674,997 A | 10/1997 | Woodard et al. |
| 5,693,785 A | 12/1997 | Woodard et al. |
| 5,705,628 A | 1/1998 | Hawkins |
| 5,777,099 A | 7/1998 | Mehra |
| 5,783,686 A | 7/1998 | Gonzalez |
| 5,804,684 A | 9/1998 | Su |

(Continued)

FOREIGN PATENT DOCUMENTS

| DE | 19801730 | 7/1999 |
| EP | 0389063 | 9/1990 |

(Continued)

OTHER PUBLICATIONS

Boom, R. et al., "Rapid and Simple Method for Purification of Nucleic", *Journal of Clinical Microbiology*, vol. 28(3), Mar. 1990, 495-503.
Bresser, J. et al., "Biological activity of mRNA immobilized on nitrocellulose in NaI,", *Proc. Natl. Acad. Sci. USA*,, 1983, 6523-6527.
Bresser, J. et al., "Laboratory Methods: Quick-Blot: Selective mRNA or DNA Immobilization from Whole Cells", 1983, 243-254.
Bresser, J. et al., "Quantitative Binding of Covalently Closed Circular DNA to Nitrocellulose in NaI,", *Analytical Biochemistry*,, 1983, 357-364.
Carter, M. "An inexpensive and simple method for DNA purifications on silica particles". *Nucleic Acids Research*, 21(4):, 1983, 1044.
Chen, C. W. et al., "Recovery of DNA Segments from Agarose Gel", *Analytical Biochemistry*,, 1980 339-341.
Costanzi, C. et al., "Fast Blots: Immobilization of DNA and RNA from Cells," *Methods in Enzymology*, 152, 1987, 582-587.
Englard, S. et al., "Precipitation Techniques", *Methods in Enzymology*, 1990, 285-300.
EP027940065.9 Communication of Notice of Opposition mailed Sep. 27, 2010.

(Continued)

*Primary Examiner* — Ethan C Whisenant

(57) ABSTRACT

The invention relates to methods for isolating and/or identifying nucleic acids. The invention also provides kits for isolating and/or identifying nucleic acids.

13 Claims, 36 Drawing Sheets

(56) References Cited

U.S. PATENT DOCUMENTS

| | | | |
|---|---|---|---|
| 5,808,041 | A | 9/1998 | Padhye et al. |
| 5,916,775 | A | 6/1999 | Hayashizaki |
| 5,972,613 | A | 10/1999 | Somack et al. |
| 5,973,137 | A | 10/1999 | Heath |
| 5,990,302 | A | 11/1999 | Kuroita et al. |
| 6,043,354 | A | 3/2000 | Hillebrand et al. |
| 6,180,778 | B1 | 1/2001 | Bastian et al. |
| 6,270,970 | B1 | 8/2001 | Smith et al. |
| 6,291,166 | B1 | 9/2001 | Gerdes et al. |
| 6,355,792 | B1 | 3/2002 | Michelsen et al. |
| 7,208,271 | B2 | 4/2007 | Bost et al. |
| 7,537,898 | B2 | 5/2009 | Bost et al. |
| 2002/0156037 | A1 | 10/2002 | Volkin et al. |
| 2007/0224630 | A1 | 9/2007 | Bost et al. |
| 2010/0021905 | A1 | 1/2010 | Bost et al. |

FOREIGN PATENT DOCUMENTS

| | | |
|---|---|---|
| EP | 0391608 | 10/1990 |
| EP | 0554034 | 8/1993 |
| EP | 0757106 | 2/1997 |
| EP | 0818461 | 1/1998 |
| EP | 0819696 | 1/1998 |
| EP | 0832897 | 4/1998 |
| EP | 0875271 | 11/1998 |
| EP | 0969090 | 1/2000 |
| EP | 1146049 | 10/2001 |
| EP | 1448799 | 11/2009 |
| WO | WO-87/06621 | 11/1987 |
| WO | WO 91/00924 | 1/1991 |
| WO | WO 92/18514 | 10/1992 |
| WO | WO 95/01359 | 1/1995 |
| WO | WO 95/04140 | 2/1995 |
| WO | WO 95/21849 | 8/1995 |
| WO | WO 96/18731 | 6/1996 |
| WO | WO 97/05248 | 2/1997 |
| WO | WO 97/10331 | 3/1997 |
| WO | WO 97/29190 | 8/1997 |
| WO | WO 97/30062 | 8/1997 |
| WO | WO 98/04730 | 2/1998 |
| WO | WO 98/26284 | 6/1998 |
| WO | WO 98/45311 | 10/1998 |
| WO | WO 98/59076 | 12/1998 |
| WO | WO 99/39009 | 8/1999 |
| WO | WO 99/40098 | 8/1999 |
| WO | WO 99/51734 | 10/1999 |
| WO | WO 99/61603 | 12/1999 |
| WO | WO 00/63362 | 10/2000 |
| WO | WO 00/70041 | 11/2000 |
| WO | WO 01/14590 | 3/2001 |
| WO | WO 02/090539 | 11/2002 |
| WO | WO 03/033739 | 4/2003 |
| WO | WO 03/046146 | 6/2003 |

OTHER PUBLICATIONS

EP027940065.9 Grounds of Appeal (Appeal No. T0335/13-3.3.08) mailed Apr. 8, 2013.
EP027940065.9 Interlocutory Decision in Opposition Proceedings (Art. 10(3)(a) and 106(2) EPC mailed Nov. 26, 2012.
EP027940065.9 Minutes in Accordance with Rule 124(4) EPC mailed Nov. 9, 2012.
EP027940065.9 Notice of Appeal mailed Feb. 6, 2013.
EP027940065.9 Patentees Response to Opponents Letter dated May 4, 2012 filed May 15, 2012.
EP027940065.9 Reply to Patentees Submission Dated Apr. 17, 2011 filed Nov. 7, 2011.
EP027940065.9 Reply Opposition Brief filed Apr. 7, 2011.
EP027940065.9 Summons to Attend Oral Proceeding Pursuant to Rule 115(1) EPC mailed Jun. 1, 2012.
EP02794065.9 Communication of a Notice of Opposition mailed Aug. 25, 2010.
EP02794065.9 Communication Pursuant to Article 96(2) mailed Feb. 6, 2007.
EP02794065.9 Communication Pursuant to Article 96(2) mailed May 9, 2006.
EP02794065.9 Communication Pursuant to Article 96(2) mailed Nov. 7, 2007.
EP02794065.9 Invitation Pursuant to Article 94(3) and Rule 71(1) mailed Mar. 16, 2009.
EP02794065.9 Search Report Mailed Nov. 3, 2005.
EP02794065.9 Supplemental Partial Search Report mailed Jan. 20, 2006.
Gillespie, D. et al., "mRNA Immobilization in NaI: Quick-Blots," *BioTechniques*, 1983, 184-192.
Gillespie, D. et al., The Role of Chaotropic Salts in Two-Phase Gene Diagnosis:, *BioEssays,*, 1984, 272-276.
Hair, M. et al., Acidity of Surface Hydroxyl Groups >>, 1970, 91-94.
Hatefi, Y. et al., "Destabilization of Membranes with Chaotropic Ions", *Methods in Enzymology*, 1974, 770-790.
JP2008282297 Office Action mailed Apr. 25, 2011, 3 pgs.
Kristensen, T. et al., "A simple and rapid preparation of M13 sequencing templates for manual and automated dideoxy sequencing", *Nucleic Acids Research*, 1987, 5507-5516.
Lee, P. et al., "Modification of a Commercially Available Method of Extracting Plasmid DNA", 1990, 386.
Lorenz, M. et al., "Adsorption of DNA to Sand and Variable Degradation Rates of Absorbed DNA", *Applied and Environmental Microbiology,*, 1987, 2948-2952.
Marko, M. A. et al., "A Procedure for the Large-Scale Isolation of Highly Purified Plasmid DNA Using Alkaline Extraction and Binding to Glass Powder," *Analytical Biochemistry*, 1982, 382-387.
McNally, et al., "A Library of Monoclonal Antibodies to *Escherichia coli* K-12 Pyruvate Dehydrogenase Complex", *Journal of Biological Chemistry* 270 (34), 1995, 19736-19743.
Melzak, K. A. et al., "Driving Forces for DNA Adsorption to Silica in Perchlorate Solutions", *Journal of Colloid and Interface Science*, 181:, 1996, 635-644.
PCT/US2002/038123 International Search Report.
U.S. Appl. No. 10/306,347 Amendment and Response to Office Action (*Ex parte Quayle* ) filed Oct. 23, 2006.
U.S. Appl. No. 10/306,347 Amendment and Response to Office Action filed Nov. 21, 2005.
U.S. Appl. No. 10/306,347 Applicants Statement of Interview Summary filed Jan. 11, 2007.
U.S. Appl. No. 10/306,347 Ex-Parte Quayle Action mailed on Aug. 24, 2006.
U.S. Appl. No. 10/306,347 Nonfinal Office Action mailed Aug. 19, 2005.
U.S. Appl. No. 10/306,347 Nonfinal Office Action mailed Mar. 8, 2006.
U.S. Appl. No. 10/306,347 Notice of Allowance and Interview Summary mailed Dec. 15, 2006.
U.S. Appl. No. 11/789,352 Amendment and Response to Nonfinal Office Action filed Sep. 6, 2008.
U.S. Appl. No. 11/789,352 Nonfinal Office Action mailed Jun. 16, 2008.
U.S. Appl. No. 11/789,352 Notice of Allowance mailed Jan. 13, 2009.
U.S. Appl. No. 12/471,292 Amendment and Response Final Office Action filed May 3, 2011.
U.S. Appl. No. 12/471,292 Amendment and Response Nonfinal Office Action filed Mar. 13, 2013.
U.S. Appl. No. 12/471,292 Amendment and Response to Nonfinal Office Action filed Oct. 8, 2010.
U.S. Appl. No. 12/471,292 Final Office Action Mailed Jan. 5, 2011.
U.S. Appl. No. 12/471,292 Nonfinal Office Action Mailed Apr. 8, 2010.
U.S. Appl. No. 12/471,292 Nonfinal Office Action mailed Dec. 19, 2012.
U.S. Appl. No. 12/471,292 Notice of Allowance mailed May 28, 2013.
Vogelstein, B., "Preparative and analytical purification of DNA from agarose", *Proceedings of the National Academy of Sciences (PNAS )*, 76, 1979, 615-619.
Willis,, E. et al., "Prep-A-GeneTM: A Superior Matrix for the Purification of DNA and DNA Fragments", 1990, 92-99.

COMPOSITIONS AND METHODS OF SELECTIVE NUCLEIC ACID ISOLATION

PRIORITY DATA

This application is a continuation of U.S. patent application Ser. No. 12/471,292, filed on May 22, 2009, which is a divisional of U.S. patent application Ser. No. 11/789,352, filed Apr. 23, 2007, which is a divisional of U.S. patent application Ser. No. 10/306,347, filed Nov. 27, 2002, which claims the benefit of U.S. Provisional Application No. 60/334,029, filed Nov. 28, 2001. Application Ser. No. 12/471,292, now U.S. Pat. Nos. 8,507,198, 10/306,347, now U.S. Pat. Nos. 7,208,271, 11/789,352, now U.S. Pat. Nos. 7,537,898, and 60/334,029 are incorporated by reference herein in their entirety for any purpose.

GRANT INFORMATION

The present inventions may have been made with support from the U.S. Government under NIST Grant No. 70NANB8H4002. The U.S. Government may have certain rights in the inventions recited herein.

FIELD OF THE INVENTION

The invention relates to methods for isolating and/or identifying nucleic acids. The invention also provides kits for isolating and/or identifying nucleic acids.

BACKGROUND OF THE INVENTION

It may be desirable to isolate nucleic acids from a biological sample. In certain instances, It would be useful to selectively isolate DNA from such a biological sample. In certain instances it would be useful to selectively isolate DNA and to selectively isolate RNA from a biological sample. Typical protocols for isolating either RNA or DNA have used selective enzymatic degradation to remove the undesired nucleic acid.

SUMMARY OF THE INVENTION

According to certain embodiments, methods of isolating DNA from a biological sample are provided. In certain embodiments, methods of isolating DNA from a biological sample comprise: selectively binding DNA to a solid phase by contacting the biological sample with the solid phase under conditions which selectively bind DNA; separating the solid phase with the bound DNA from an unbound portion of the biological sample; and isolating the DNA from the solid phase.

According to certain embodiments, the conditions which selectively bind DNA comprise using a binding buffer comprising: an alkaline pH; and a large anion, wherein the large anion is at least as large as a bromide ion.

According to certain embodiments, methods of isolating DNA and RNA from a biological sample are provided, comprising: selectively binding DNA to a first solid phase by contacting the biological sample with the first solid phase under conditions which selectively bind DNA; separating the first solid phase with the bound DNA from a first unbound portion of the biological sample; isolating the DNA from the first solid phase; and isolating RNA from the first unbound portion of the biological sample.

According to certain embodiments, the isolating of the RNA from the first unbound portion of the biological sample comprises: exposing the first unbound portion of the biological sample to a second solid phase under conditions which bind RNA to the second solid phase; separating the second solid phase with bound RNA from the second portion of the biological sample; and isolating the RNA from the second solid phase.

According to certain embodiments, methods of isolating nucleic acid from a biological sample are provided, comprising: binding nucleic acid to a first solid phase by contacting the biological sample with the first solid phase under conditions which bind both DNA and RNA; separating the first solid phase with bound nucleic acid from a first unbound portion of the biological sample; eluting RNA from the first solid phase with bound nucleic acid under conditions which selectively bind DNA; removing the first solid phase with bound DNA from a first eluate; and isolating the DNA from the first solid phase.

According to certain embodiments, the conditions which selectively bind DNA comprise using a binding buffer comprising: an alkaline pH; and a large anion, wherein the large anion is at least as large as a bromide ion.

According to certain embodiments, the method of isolating nucleic acid from a biological sample further comprises: exposing the first eluate to a second solid phase under conditions which bind RNA to the second solid phase; separating the second solid phase with the bound RNA from a second eluate; and isolating the RNA from the second solid phase.

According to certain embodiments, isolating nucleic acid from a solid phase comprises eluting the nucleic acid from the solid phase.

According to certain embodiments, methods of identifying DNA in a biological sample are provided. In certain embodiments, methods of identifying DNA in a biological sample comprise: selectively binding DNA to a solid phase by contacting the biological sample with the solid phase under conditions which selectively bind DNA; separating the solid phase with the bound DNA from an unbound portion of the biological sample; and identifying the DNA bound to the solid phase. According to certain embodiments, the identifying the nucleic acid on a solid phase comprises amplifying the nucleic acid bound to the solid phase.

According to certain embodiments, a kit is provided, comprising: a buffer with an alkaline pH; a large anion, wherein the large anion is at least as large as a bromide ion; and a solid phase.

According to certain embodiments, a kit is provided comprising: a solid phase; a nucleic acid binding buffer, wherein both DNA and RNA bind the solid phase under conditions generated by the nucleic acid binding buffer; and a selective DNA binding buffer, wherein the conditions generated by the selective DNA binding buffer allow selective binding of DNA to the solid phase.

DETAILED DESCRIPTION OF CERTAIN EMBODIMENTS

Figure 1:
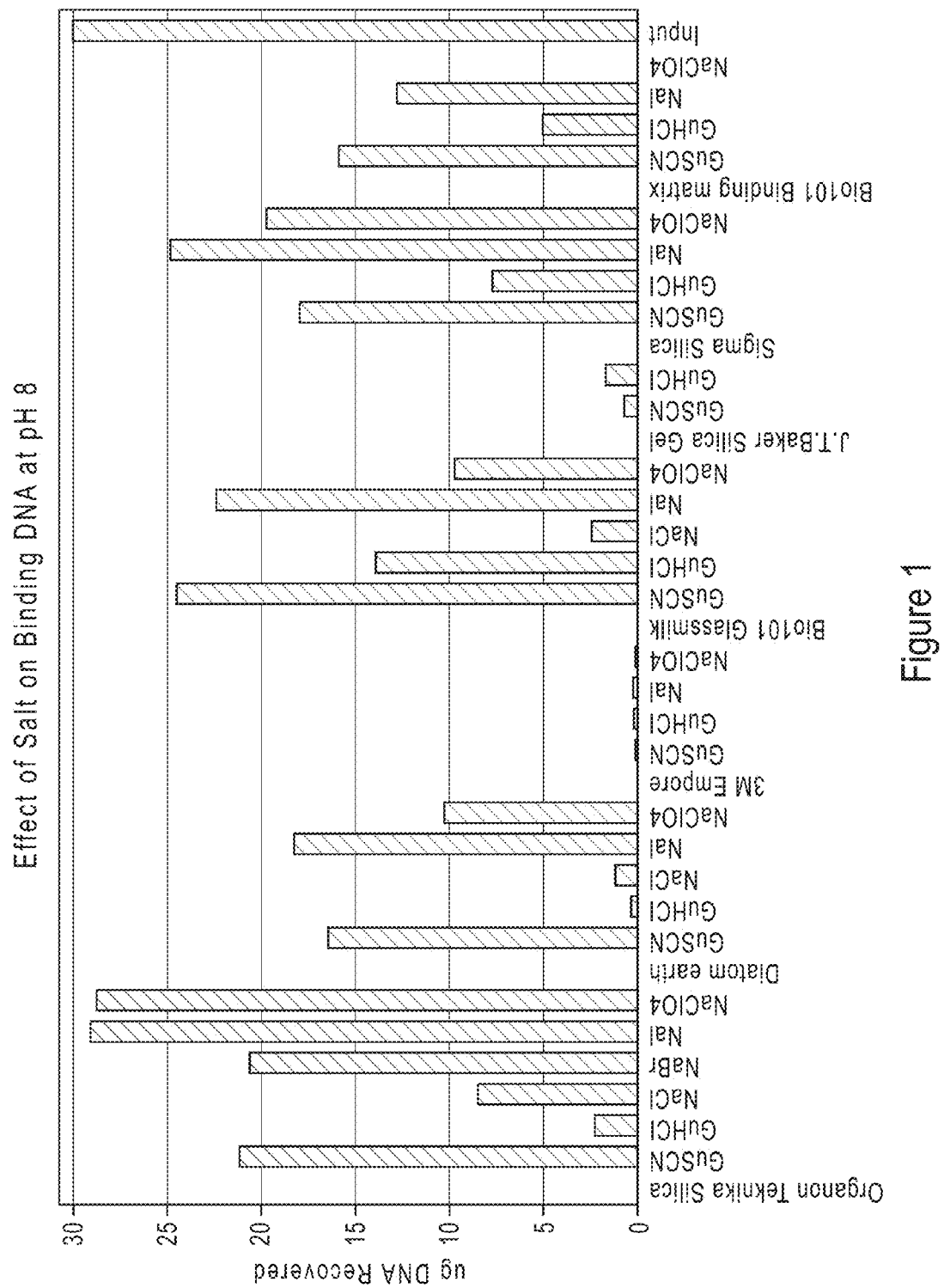
FIG. 1 shows the effects of various salts on the binding of DNA to various solid phases at pH 8.

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

DEFINITIONS

The term "biological sample" is used in a broad sense and is intended to include a variety of biological sources that contain nucleic acids. Such sources include, without limitation, whole tissues, including biopsy materials and aspirates; in vitro cultured cells, including primary and secondary cells, transformed cell lines, and tissue and cellular explants; whole blood, red blood cells, white blood cells, and lymph; body fluids such as urine, sputum, semen, secretions, eye washes and aspirates, lung washes, cerebrospinal fluid, abscess fluid, and aspirates. Included in this definition of "biological sample" are samples processed from biological sources, including but not limited to cell lysates and nucleic acid-containing extracts. Any organism containing nucleic acid may be a source of a biological sample, including, but not limited to, any eukaryotes, eubacteria, archaebacteria, or virus. Fungal and plant tissues, such as leaves, roots, stems, and caps, are also within the scope of the present invention. Microorganisms and viruses that may be present on or in a biological sample are within the scope of the invention.

The term "buffer," as used herein, refers to aqueous solutions or compositions that resist changes in pH when acids or bases are added to the solution. This resistance to pH change is due to the solution's buffering action. Solutions exhibiting buffering activity are referred to as buffers or buffer solutions. Buffers typically do not have an unlimited ability to maintain the pH of a solution or composition. Rather, typically they are able to maintain the pH within certain ranges, for example between pH 5 and pH 7. See, generally, C. Mohan, Buffers, A guide for the preparation and use of buffers in biological systems, Calbiochem, 1999. Exemplary buffers include, but are not limited to, MES ([2-(N-Morphilino)ethanesulfonic acid]), ADA (N2-Acetamido-2-iminodiacetic acid), and Tris ([tris(Hydroxymethyl)aminomethane]; also known as Trizma); Bis-Tris; ACES; PIPES; and MOPS.

Buffers that maintain the pH within a certain pH range, for example, between pH 5 and pH 7, and similar terms as used herein, are intended to encompass any buffer that exhibits buffering action at some point within the stated pH range. Thus, that term encompasses buffers that do not exhibit buffering capacity within the entire stated range, and buffers with buffering capacity that extend beyond the stated range. For example, solution A may exhibit buffering capacity between pH 5.2 and 6.7, solution B may exhibit buffering capacity between 6.0 and 8.0. For purposes of this invention, both of those solutions would be considered buffers that maintain the pH within the range of pH 5.0 to pH 7.0. The skilled artisan will be able to identify an appropriate buffer for maintaining the pH between a specified range using a buffer table. Buffer tables can be found in, among other places, the Calbiochem 2000-2001 General Catalog at pages 81-82, and the Sigma 2000-2001 Biochemicals and Reagents for Life Science Research Catalog at page 1873, both of which are expressly incorporated by reference.

The term "isolating" nucleic acid refers to the recovery of nucleic acid molecules from a source. While it is not always optimal, the process of recovering nucleic acid may also include recovering some impurities such as protein. It includes, but is not limited to, the physical enrichment of nucleic acid molecules from a source. The term "isolating" may also refer to the duplication or amplification of nucleic acid molecules, without necessarily removing the nucleic acid molecules from the source.

The term "salt" as used herein, refers to a compound produced by the interaction of an acid and a base. Exemplary salts include, but are not limited to, sodium chloride (table salt), sodium iodide, sodium bromide, lithium bromide, lithium iodide, potassium phosphate, sodium bicarbonate, and the like. In water and other aqueous solutions, salts typically dissociate into an "anion" or negatively charged subcomponent, and a "cation" or positively charge subcomponent. For example, when sodium chloride (NaCl) is dissolved in water, it dissociates into a sodium cation (Na.sup.+) and a chloride anion (Cl.sup.−). Examplary salts are discussed, e.g., in Waser, Jurg, Quantitative Chemistry, A Laboratory Text, W. A. Benjamin, Inc., New York, page 160, (1966).

The term "nucleic acid," as used herein, refers to a polymer of ribonucleosides or deoxyribonucleosides typically comprising phosphodiester linkages between subunits. Other linkages between subunits include, but are not limited to, methylphosphonate, phosphorothioate, and peptide linkages. Such nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Solid phase components (also called solid phases) that are capable of binding to nucleic acids released from a biological sample include a variety of materials that are capable of binding nucleic acids under suitable conditions. Exemplary solid phase components include, but are not limited to, silica particles, silicon dioxide, diatomaceous earth, glass, alkyl-silica, aluminum silicate, borosilicate, nitrocellulose, diazotized paper, hydroxyapatite, nylon, metal oxides, zirconia, alumina, diethylaminoethyl- and triethylaminoethyl-derivatized supports (Chromegabond SAX, LiChrosorb-AN, Nucleosil SB, Partisil SAX, RSL Anion, Vydac TP Anion, Zorbax SAX, Nucleosil NMe.sub.2, Aminex A-series, Chromex, and Hamilton HA Ionex SB, DEAE sepharose, QAE sepharose), hydrophobic chromatography resins (such phenyl- or octyl-sepharose), and the like.

The term "selective binding" with regard to nucleic acid refers to binding of a type or species of nucleic acid (e.g., DNA) to a solid phase under conditions in which other types or species of nucleic acid (e.g., RNA) bind less efficiently. For example, conditions for binding may be said to be selective for DNA when the amount of DNA bound to a solid phase is greater than the amount of RNA, when the DNA and RNA are in equimolar ratios in solution. Further, conditions for the binding of DNA to a solid phase may be said to be selective when the efficiency of binding of DNA to a solid phase is unaffected by the amount of RNA in solution with the DNA.

Exemplary Embodiments

A. According to certain embodiments, methods of isolating DNA from a biological sample are provided, which comprise: selectively binding DNA to a solid phase by contacting the biological sample with the solid phase under conditions which selectively bind DNA; separating the solid phase with the bound DNA from an unbound portion of the biological sample; and isolating the DNA from the solid phase.

According to certain embodiments, methods of identifying DNA in a biological sample are provided. In certain embodiments, methods of identifying DNA in a biological sample comprise: selectively binding DNA to a solid phase by contacting the biological sample with the solid phase under conditions which selectively bind DNA; separating the solid phase with the bound DNA from an unbound portion of the biological sample; and identifying the DNA bound to the solid phase. According to certain embodiments, the identifying the DNA bound to the solid phase comprises amplifying the DNA bound to the solid phase.

According to certain embodiments, the solid phase is a siliceous material. In certain embodiments, the siliceous material is selected from a group comprising silica, silica dioxide, diatomaceous earth, glass, Celite, and silica gel. In certain embodiments, the solid phase is in a form selected from a group comprising a particle, a bead, a membrane, a frit, and a side of a container. Exemplary, but nonlimiting, examples of solid phases are discussed in U.S. Pat. Nos. 4,648,975; 4,923,978; 5,075,430; 5,175,271; 5,234,809; 5,438,129; 5,658,548; 5,804,684; and 5,808,041; European Application Nos. EP 0 391 608 and EP 0 757 106; and PCT Publication Nos. WO 87/06621; WO 91/00924; WO 92/18514; WO 97/30062; WO 99/51734; and WO 99/40098.

According to certain embodiments, the conditions which selectively bind DNA comprise using a binding buffer comprising: an alkaline pH; and a large anion, wherein the large anion is at least as large as a bromide ion. In certain embodiments, the large anion is selected from at least one of a group comprising picrate, tannate, tungstate, molybdate, perchlorate, and sulfosalicylate. In certain embodiments, the large anion is selected from at least one of a group comprising trichloroacetate, tribromoacetate, thiocyanate, and nitrate. In certain embodiments, the large anion is selected from at least one of a group comprising iodide and bromide. In certain embodiments, the alkaline pH is equal to, or above 8.0. In certain embodiments, the alkaline pH is equal to, or above 9.0. In certain embodiments, the alkaline pH is equal to, or above 10.0. In certain embodiments, the alkaline pH is any pH range or point between 8.0 and 12.0.

In certain embodiments, the isolating the DNA from the solid phase comprises eluting the DNA.

B. According to certain embodiments, methods of isolating DNA and RNA from a biological sample are provided, which comprise: selectively binding DNA to a first solid phase by contacting the biological sample with the first solid phase under conditions which selectively bind DNA; separating the first solid phase with the bound DNA from a first unbound portion of the biological sample; isolating the DNA from the first solid phase; and isolating RNA from the first unbound portion of the biological sample. In certain embodiments, the isolating the DNA from the first solid phase comprises eluting the DNA.

According to certain embodiments, methods of identifying DNA and RNA in a biological sample are provided, which comprise: selectively binding DNA to a first solid phase by contacting the biological sample with the first solid phase under conditions which selectively bind DNA; separating the first solid phase with the bound DNA from a first unbound portion of the biological sample; identifying the DNA bound to the first solid phase; and identifying the RNA from the first unbound portion of the biological sample. In certain embodiments, the isolating the DNA from the first solid phase comprises eluting the DNA. In certain embodiments, the identifying the DNA bound to the first solid phase comprises amplifying the DNA bound to the first solid phase.

One of ordinary skill will appreciate that there are many methods of identifying nucleic acid (both DNA and RNA) bound to a solid phase, according to certain embodiments. Such methods include, but are not limited to, hybridization to labeled probes, reverse transcription, mass spectrometry, and detection by a reaction of the bound DNA with a label, e.g., detection of fluorescence following the addition of a DNA-binding fluorophore.

According to certain embodiments, the isolating of the RNA from the first unbound portion of the biological sample comprises: exposing the first unbound portion of the biological sample to a second solid phase under conditions which bind RNA to the second solid phase; separating the second solid phase with bound RNA from the second portion of the biological sample; and isolating the RNA from the second solid phase by eluting the RNA.

According to certain embodiments, the conditions which bind RNA to the second solid phase comprise a neutral or acidic pH. In certain embodiments, the conditions which bind RNA to the second solid phase comprise reducing the pH to 8.0 or below. In certain embodiments, the conditions which bind RNA to the second solid phase comprise use of a salt with an anion smaller than bromide.

According to certain embodiments, the second solid phase is selected from any of the materials discussed above to the first solid phase in A above. The second solid phase may be the same material as the first solid phase or it may be different material.

According to certain embodiments, the conditions which selectively bind DNA comprise using a binding buffer comprising: an alkaline pH; and a large anion, wherein the large anion is at least as large as a bromide ion. Conditions which selectively bind DNA for these methods may comprise the conditions discussed above for selectively binding DNA in section A.

As a non-limiting example, one may add a buffer or salt to a cell lysate, making the cell lysate very alkaline. A solid phase, such a silica bead, would then be exposed to the alkaline lysate. DNA selectively binds to the bead, which is then removed. Another buffer or salt is added to the alkaline lysate to make the lysate neutral in pH. A second solid phase is added to the neutral lysate, and the RNA in the lysate binds to the second solid phase. The DNA bound to the first solid phase is then eluted with a neutral or alkaline, low salt buffer. The second solid phase is removed from the neutral lysate, and the RNA is eluted from the second solid phase with a neutral or alkaline, low salt buffer.

C. According to certain embodiments, methods of isolating nucleic acid from a biological sample are provided, which comprise: binding nucleic acid to a first solid phase by contacting the biological sample with the first solid phase under conditions which bind both RNA and DNA; separating the first solid phase with bound nucleic acid from a first unbound portion of the biological sample; eluting RNA from the first solid phase with bound nucleic acid under conditions which selectively bind DNA; removing the first solid phase with bound DNA from a first eluate; and isolating the DNA from the first solid phase.

According to certain embodiments, the isolating the DNA from the first solid phase comprises eluting the DNA from the first solid phase.

According to certain embodiments, methods of identifying nucleic acid in a biological sample are provided, which comprise: binding nucleic acid to a first solid phase by contacting the biological sample with the first solid phase under conditions which bind both RNA and DNA; separating the first solid phase with bound nucleic acid from a first unbound portion of the biological sample; eluting RNA from the first solid phase with bound nucleic acid under conditions which selectively bind DNA; removing the first solid phase with bound DNA from a first eluate of the biological sample; and identifying the DNA bound to the first solid phase. According to certain embodiments, the identifying the DNA bound to the first solid phase comprises amplifying the DNA bound to the first solid phase.

One of ordinary skill will appreciate that there are many methods of identifying nucleic acid (both DNA and RNA) bound to a solid phase, according to certain embodiments. Such methods include, but are not limited to, hybridization to labeled probes, reverse transcription, mass spectrometry, and detection by a reaction of the bound DNA with a label, such as detection of fluorescence following the addition of a DNA-binding fluorophore.

According to certain embodiments, the first solid phase is selected from any of the materials discussed above to the first solid phase in A above.

According to certain embodiments, the conditions which selectively bind DNA comprise using a binding buffer comprising: a buffer with an alkaline pH; and a large anion, wherein the large anion is at least as large as a bromide ion.

Conditions which selectively bind DNA for these methods may comprise the conditions discussed above for selectively binding DNA in section A.

According to certain embodiments, the method of isolating nucleic acid from a biological sample further comprises: exposing the first eluate to a second solid phase under conditions which bind RNA to the second solid phase; separating the second solid phase with the bound RNA from a second eluate of the biological sample; and isolating the RNA from the second solid phase.

According to certain embodiments, the isolating the RNA from the second solid phase comprises eluting the RNA. According to certain embodiments, the isolating the RNA from the second solid phase comprises amplifying the RNA bound to the second solid phase.

According to certain embodiments, the second solid phase is selected from any of the materials discussed above to the first solid phase in A above. The second solid phase may be the same material as the first solid phase or it may be different material.

According to certain embodiments, the conditions which selectively bind DNA comprise using a binding buffer comprising: an alkaline pH; and a large anion, wherein the large anion is at least as large as a bromide ion. Conditions which selectively bind DNA for these methods may comprise the conditions discussed above for selectively binding DNA in section A. In certain embodiments, the conditions which bind RNA to the second solid phase comprise a neutral or acidic pH.

In certain embodiments, the conditions which bind RNA to the second solid phase comprise reducing the pH to 8.0 or below. In certain embodiments, the conditions which bind RNA to the second solid phase comprise use of a salt with an anion smaller than bromide.

As a non-limiting example, a solid phase, such a silica bead, would be exposed to a cell lysate. Nucleic acid, both DNA and RNA, then binds to the solid phase, which is then removed. The solid phase is then placed in a high pH buffer, which allows the RNA to elute from the solid phase, but keeps the DNA bound to the solid phase. The solid phase is then removed, and placed in a low salt buffer, which elutes the DNA.

D. According to certain embodiments, a kit is provided, which comprises: a buffer with an alkaline pH; a large anion, wherein the large anion is at least as large as a bromide ion; and a solid phase. In certain embodiments, the large anion is selected from any of the large anions discussed in section A. In certain embodiments, the alkaline pH is equal to, or above 8.0. In certain embodiments, the alkaline pH is equal to, or above 9.0. In certain embodiments, the alkaline pH is equal to, or above 10.0. According to certain embodiments, the solid phase is selected from any of the materials discussed above to the solid phase in A above.

E. According to certain embodiments, a kit is provided, which comprises: a solid phase; a nucleic acid binding buffer, wherein both DNA and RNA bind the solid phase under conditions generated by the nucleic acid binding buffer; and a selective DNA binding buffer, wherein the conditions generated by the selective DNA binding buffer allow selective binding of DNA to the solid phase. The conditions which selectively bind DNA are those discussed in section A, above. In certain embodiments, the kit further comprises an RNA binding buffer, wherein the conditions generated by the RNA binding buffer allow RNA to bind to a solid phase. Conditions which allow the binding of RNA are those discussed in section B, above. In certain embodiments, the selective binding buffer has a pH equal to, or above 8.0. In certain embodiments, the selective binding buffer has a pH equal to, or above 9.0. In certain embodiments, the selective binding buffer has a pH equal to, or above 10.0. According to certain embodiments, the solid phase is selected from any of the materials discussed above to the solid phase in A above. In certain embodiments, the nucleic acid binding buffer has a pH equal to, or below 8.0.

EXAMPLES

The following examples illustrate certain embodiments of the invention, and do not limit the scope of the invention in any way.

The following terms, abbreviations, and sources apply to the materials discussed throughout Examples 1 to 4.

These substrates were obtained from the following sources: Silica (Organon Teknika, Product Number 82951, Lot 00030302), Diatomaceous Earth (Sigma, Product Number D-3877, Lot 128H3702), Empore Filter Aid 400 (3M, Product Number 56221-746, Lot 990020), Silica Gel (JT Baker, Product Number 3405-01, Lot N36338), Silicon dioxide (Sigma, Product Number S-5631, Lot 58H0154), Binding Matrix (BIO-101, Product Number 6540-408, Lot Number 6540-408-0B13), Glassmilk Spin Buffer #4 (BIO 101, Product Number 2072-204, Lot Number 2072-204-8A17), Davisil Grade 643 Silica Gel (Spectrum, Product Number Sil 66, Lot NE 0387), and Uniform Silica Microspheres (Bangs Laboratories, Inc. Catalog Code SS05N, Inv # L0002188).

Abbreviations or names of the following reagents and sources for them are as follows: guanidine hydrochloride (Sigma, Lot 38H5432), guanidine thiocyanate (Sigma, Product Number G-9277), sodium iodide (Aldrich Chemical Company, Product Number 38, 311-2, Lot Number 07004TS), sodium perchlorate (Aldrich Chemical Company, Product Number 41, 024-1, Lot KU 06910HU), sodium bromide (Aldrich, Product Number 31050-6, Lot 11805KR), sodium chloride (Aldrich Chemical Company, Product Number 33, 251-4, Lot Number 16524CS), Tris (Trizma base, Tris[Hydroxymethyl]aminomethane, Sigma, Product Number T-6791, Lot Number 1261-15738)—pH 8, MES (2-[N-Morpholino]ethanesulfonic acid, Sigma, product number M-5287, lot number 58H5411)—pH 6.0, AMP (2-amino-2-methyl-1-propanol, Sigma, Product Number 221)—pH 10, Hepes (n-[2hydroxyethyl]piperazine—N'-[2-ethane sulfonic acid], Sigma, product number H-4034, lot number 19H54101), ethanol (Ethyl alcohol, absolute, Aldrich, catalog number E702-3), HCl (Sigma, Product Number H-7020, Lot Number 97H3562), sodium hydroxide (Sigma, Product Number S-8045, Lot Number 127H0531 and 69H1264), ammonium bifluoride (ammonium hydrogen fluoride, Aldrich Product Number 22, 482-0), nitric acid (Aldrich, Product number 22571-1, lot number 00261 A1), and ammonium hydroxide (Aldrich product number 22, 122-8, lot number 02308KR).

Nucleic acids and tissue samples and sources for them are as follows: calf thymus genomic DNA (deoxyribonucleic acid, type 1, highly polymerized from calf thymus, Sigma, Product Number D-1501, Lot 87H7840); rat liver total RNA (Biochain Institute, lot numbers A304057, A305062, or A306073); and whole blood (Blood Centers of the Pacific).

The spectrophotometry was performed with a Hewlett-Packard Model 8453 Spectrophotometer.

Gel electrophoresis of nucleic acid samples in Examples 12 to 14 was carried out using SeaKem® agarose (Teknova); 1.times.TBE (89 mM Tris, 89 mM Boric Acid, 2 mM EDTA, Teknova, catalog number 0278-1 L, lot number 17F801); and 0.5 .mu.g/ml ethidium bromide buffer (BIO-RAD). Molecular weight markers used in electrophoresis were an AmpliSize DNA molecular weight standard (BIO-RAD), a High Molecular Weight DNA Marker (Gibco BRL), and an RNA ladder (GIBCO BRL).

Example 1

Silica and glass matrices from a variety of suppliers were evaluated for their ability to bind genomic DNA using different salts at pH 8.

Silica (Organon Teknika), Diatomaceous Earth, Empore Filter Aid 400, J. T. Baker Silica Gel, Silicon dioxide, Binding Matrix, and Glassmilk Spin Buffer #4 were used for the following example. Prior to use, all particles (except the Silica from Organon Teknika) were prepared as follows: the particles were washed once with 4-8 volumes of 1 N HCl, twice with 4-8 volumes of water, once with 4-8 volumes of 1 N NaOH, twice with 4-8 volumes of water, once with 4-8 volumes of ethanol, and four times with 4-8 volumes of water. As used herein, one "volume" of water or ethanol referres to an amount of water or ethanol equal in mass to the mass of the particles being washed. The Binding Matrix and Glassmilk from BIO-101 were washed 4 times with at least 4 volumes of water before being treated with HCl, NaOH, and ethanol (as described above). The Silica particles were used as supplied. Diatomaceous Earth, Empore Filter Aid 400, Silica Gel, and Silicon dioxide were stored as a 200 mg/ml (20%) slurry in water. The Binding Matrix particles were stored as a 580 mg/ml (58%) slurry in water and the Glassmilk particles were stored as a 373 mg/ml (37%) slurry in water.

Calf thymus DNA was used as the source of the genomic DNA. Sheared genomic DNA used in the following examples was prepared as follows. The DNA was resuspended at approximately 10 mg/ml in water. The DNA was then sheared by passing the material four times through a 20 G 1 1/2 needle, three times through a 21 G 1 1/2 gauge needle, 22 G 1 1/2 gauge needle, and once through a 26 G 1 1/2 gauge needle.

Each solid phase and buffer combination shown in FIG. 1 was assayed once. Sheared calf thymus DNA (25 .mu.g of DNA, 50 .mu.l of a 0.5 mg/ml concentration) was added to 1.5 ml microcentrifuge tubes containing 0.45 ml of one of the following buffers: (1) 50 mM Tris-HCl, pH 8, 4.75 M guanidine thiocyanate; (2) 50 mM Tris HCl, pH 8; 4.75 M guanidine hydrochloride; (3) 50 mM Tris HCl, pH 8; 4.75 M Sodium chloride; (4) 50 mM Tris-HCl, pH 8, 4.75 M sodium bromide; (5) 50 mM Tris-HCl, pH 8, 4.75M sodium iodide; or (6) 50 mM Tris-HCl, pH 8, 4.75 M sodium perchlorate. The nucleic acid was incubated for up to 10 minutes at ambient temperature in the buffered solution, with occasional mixing. Those mixtures were incubated for 10 minutes at ambient temperature with occasional mixing. Following the binding incubation, the particles were centrifuged (15,800.times.g, 1 minute) and washed twice with 0.5 ml of the binding buffer that had been used for the binding incubation. Subsequently, the particles were washed three to four times with 0.5 ml of 70% ethanol.

Following the last ethanol wash, the particles were allowed to air dry at ambient temperature or at 56.degree. C. for 5-10 minutes. The bound nucleic acid was first eluted with 0.25 ml of 10 mM Tris, pH 9 for 5 minutes at 56.degree. C. with constant mixing and the eluted nucleic acid was collected. Any residual nucleic acid bound to the particles was subsequently eluted with 0.25 ml of 0.1 N NaOH at 56.degree. C. for 5 minutes with constant mixing and the eluted nucleic acid was collected. The amount of nucleic acid was quantified by spectrophotometry. The results are shown in FIG. 1.

At pH 8, the effect of salt composition on DNA binding appeared to be a function of the source of the solid phase. For a particular matrix, the recovery of DNA varied up to 43-fold, depending on the choice of salt. The preferred anions for most of the matrices in this work were the bulky anions thiocyanate, bromide, iodide, and perchlorate. In general, recovery of DNA was poor with salts containing the less bulky chloride anion. A comparison of the effect of GuHCl and GuSCN on DNA binding demonstrateed greater DNA binding in the presence of the larger thiocyanate anion.

Example 2

The solid phases used in the present example were prepared as described in Example 1. Sheared genomic DNA from calf thymus was prepared as described in Example 1.

Each solid phase and buffer combination was assayed once. Sheared calf thymus DNA (25 .mu.g of DNA, 50 .mu.l of a 0.5 mg/ml concentration) was added to a 1.5 ml microcentrifuge tube containing 0.45 ml of either (1) 50 mM Tris-HCl, pH 8 and 4.75 M guanidine thiocyanate; or (2) 50 mM Tris-HCl, pH 8 and 4.75 M guanidine hydrochloride. Nucleic acid was incubated up to 10 minutes at ambient temperature in the buffered solution, with occasional mixing. Each of the seven solid phases (10-187 mg) was added separately to each of the two buffered nucleic acid solutions so that there were 14 containers with each combination of the individual solid phases and buffers. Those mixtures were incubated for 10 minutes at ambient temperature with occasional mixing. Following the binding incubation, the particles were centrifuged (15,800.times.g, 1 minute) and washed twice with 0.5 ml of the binding buffer that had been used for the binding incubation. Subsequently, the particles were washed three to four times with 0.5 ml of 70% ethanol.

Figure 2:
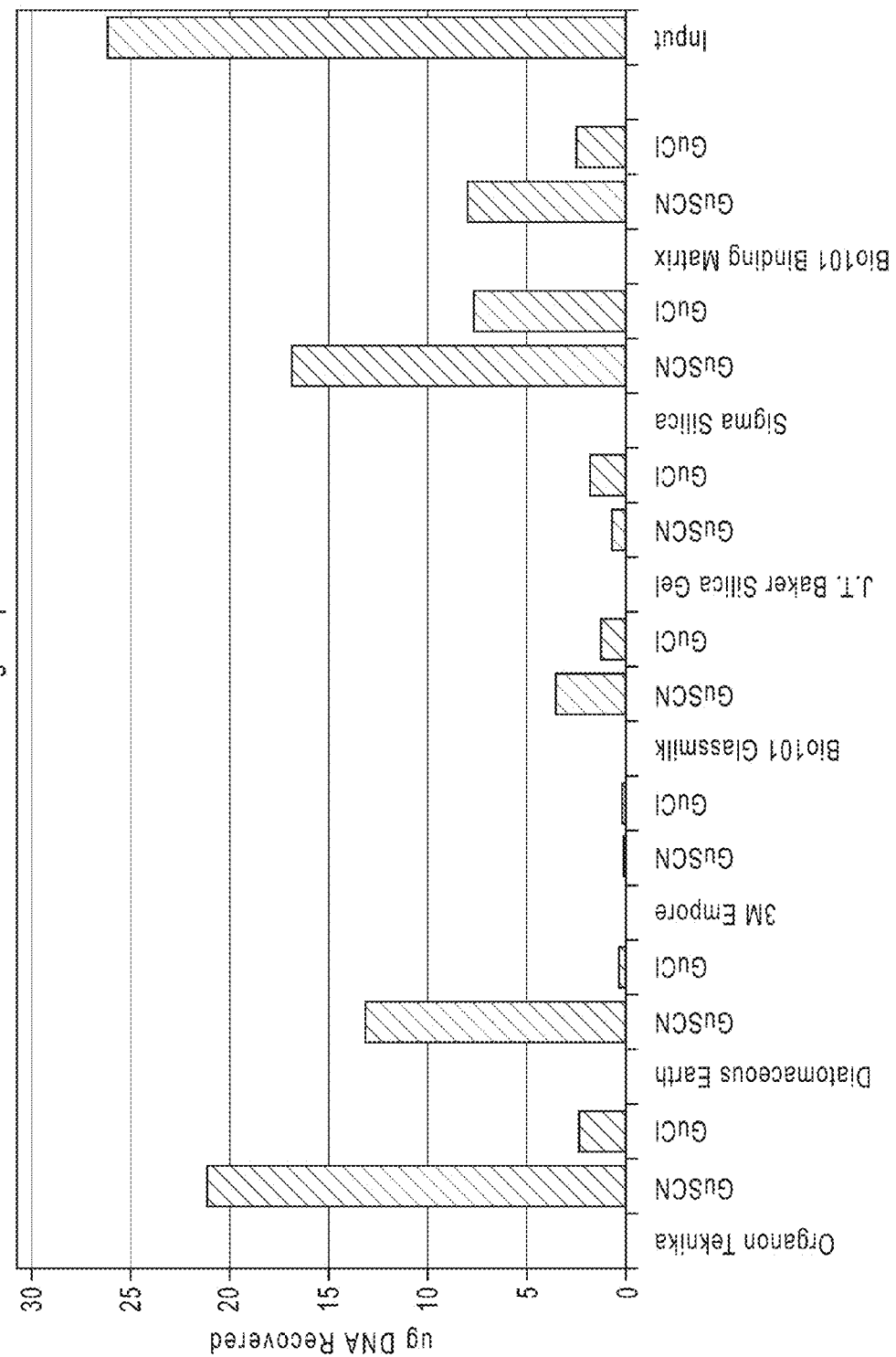
FIG. 2 compares the binding of DNA to various solid phases at pH 8 in the presence of either chloride or thiocyanate.

Following the last ethanol wash, the particles were allowed to air dry at ambient temperature or at 56.degree. C. for 5-10 minutes. The bound nucleic acid was first eluted with 0.25 ml of 10 mM Tris, pH 9 for 5 minutes at 56.degree. C. with constant mixing and the eluted nucleic acid was collected. Any residual nucleic acid bound to the particles was subsequently eluted with 0.25 ml of 0.1 N NaOH at 56.degree. C. for 5 minutes with constant mixing and the eluted nucleic acid was collected. The amount of nucleic acid was quantified by spectrophotometry. The results are shown in FIG. 2. In general, recovery in the presence of thiocyanate appeared superior to recovery in the presence of chloride ions.

Example 3

The binding characteristics of RNA to silica and glass solid phases from a variety of suppliers were evaluated using different salts at pH 8. Silica, Diatomaceous Earth, Binding Matrix, and Glassmilk Spin Buffer #4 were used for the following studies. The solid phase particles were prepared as described in Example 1.

Each solid phase and buffer combination was assayed once. Rat liver total RNA (15 .mu.g of RNA, 6 .mu.l of a 2.5 mg/ml concentration in water) was added to a 1.5 ml microcentrifuge tube containing 0.45 ml of one of the following buffers: (1) 50 mM Tris-HCl, pH 8, 4.75 M guanidine thiocyanate; (2) 50 mM Tris HCl, pH 8; 4.75 M guanidine hydrochloride; (3) 50 mM Tris HCl, pH 8; 4.75 M sodium chloride; or (4) 50 mM Tris HCl, pH 8; 4.75 M sodium iodide. Nucleic acid was incubated up to 5 minutes at ambient temperature in the buffered solution, with occasional mixing. Those mixtures were incubated 10 minutes at ambient temperature with occasional mixing.

Figure 3:
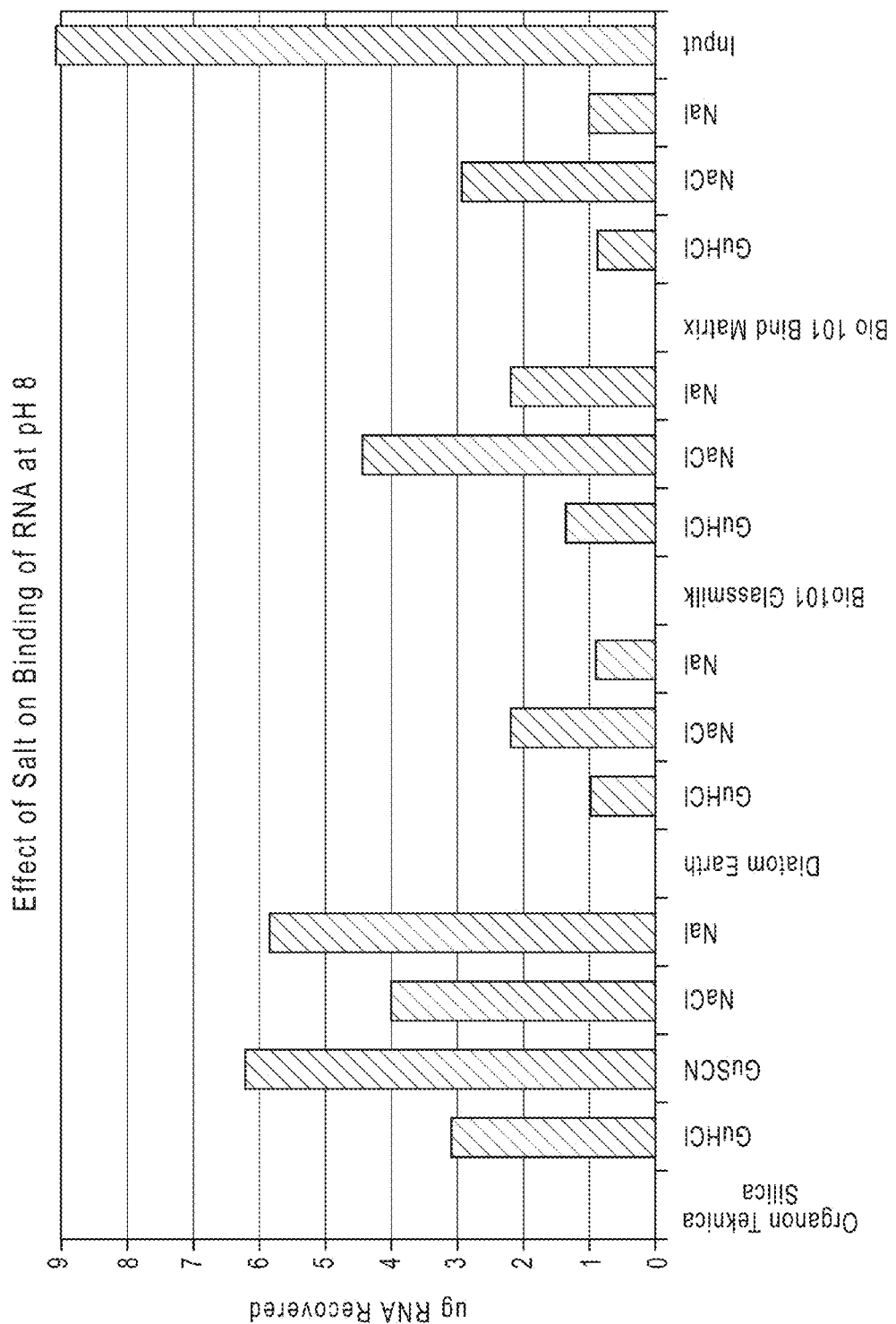
FIG. 3 shows the effects of various salts on the binding of RNA to various solid phases at pH 8.

Following the binding incubation, the particles were centrifuged (15,800.times.g, 1 minute) and washed twice with 0.5 ml of the binding buffer that had been used for the binding incubation. Subsequently, the particles were washed two or four times with 0.5 ml of 70% ethanol. The particles which were washed twice with ethanol were then washed once with 0.5 ml of acetone and were allowed to dry for 5 minutes at 56.degree. C. The bound nucleic acid was first eluted with 0.25 or 0.275 ml of 50 mM Tris, pH 9 for 5 minutes at 56.degree. C. with constant mixing and the eluted nucleic acid was collected. Any residual nucleic acid was eluted with 0.25 or 0.275 ml of 0.1 N NaOH at 56.degree. C. for 5 minutes with constant mixing and the eluted nucleic acid was collected. The amount of nucleic acid was quantified by spectrophotometry. The results are shown in FIG. 3.

In contrast to the results found with DNA, recovery of RNA when bound to the solid phase at pH 8 did not appear to show a strong dependence on salt composition. The selection of salt resulted in less than a threefold variation in the recovery of RNA for a particular matrix.

Figure 4:
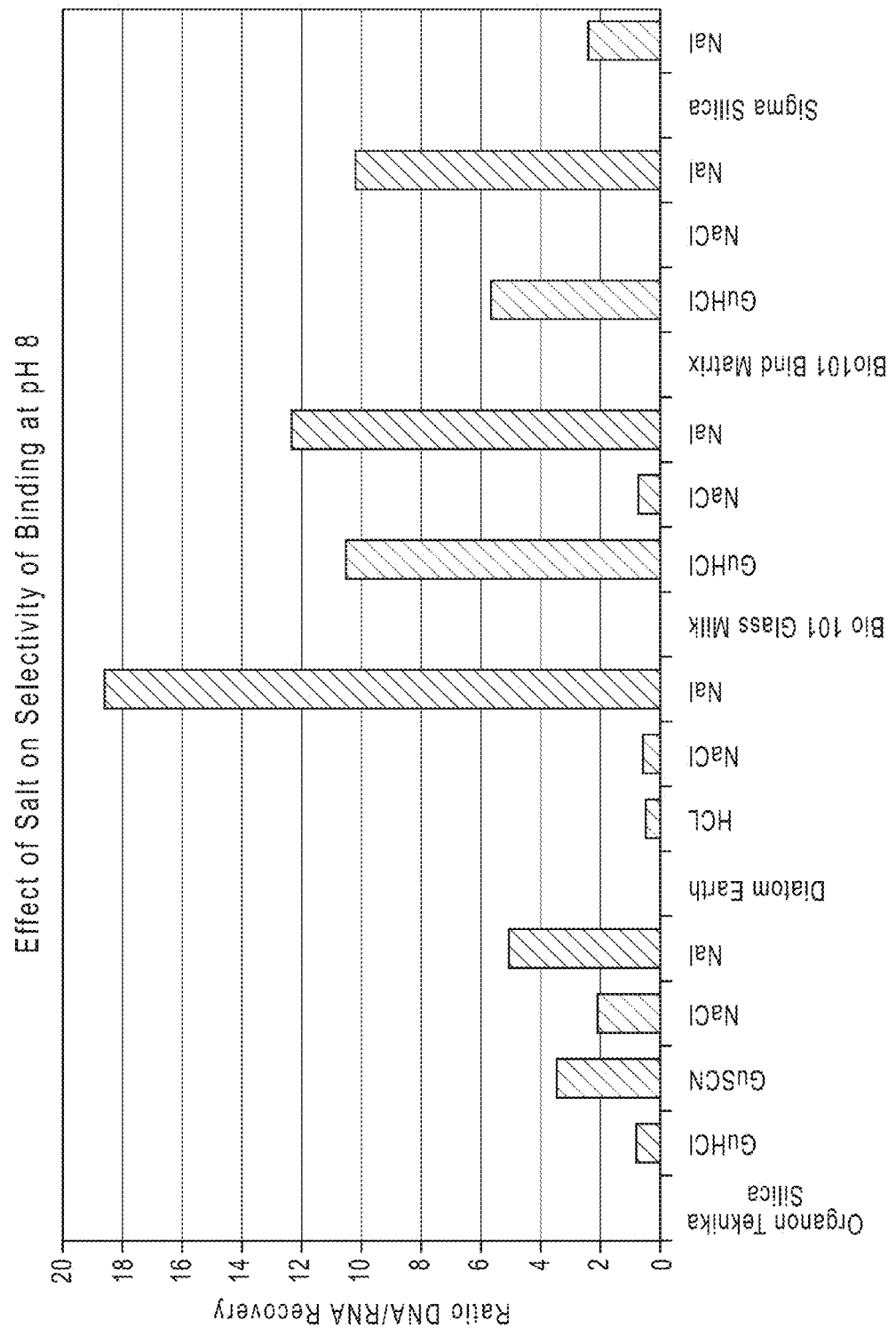
FIG. 4 shows the effects of various salts on the selectivity of DNA binding to various solid phases, expressed as a ratio of DNA to RNA recovery.
Figure 5A:
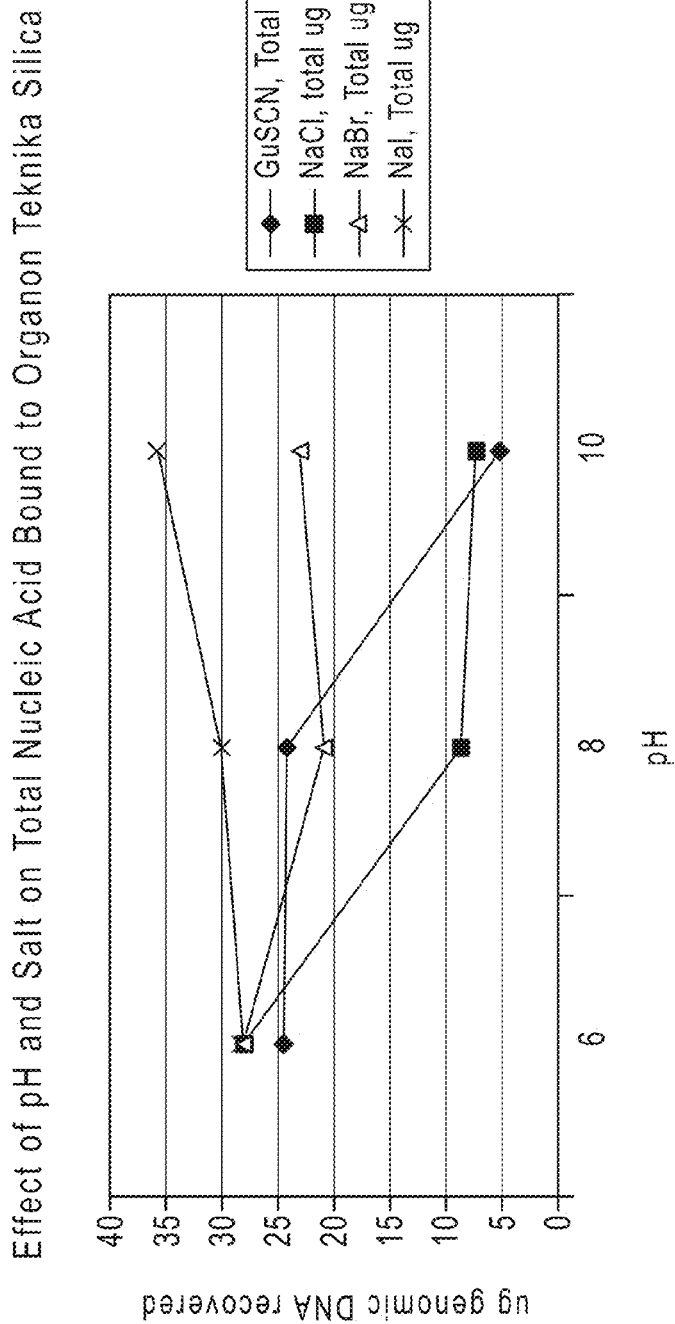
FIG. 5(*a*) shows the effects of various salts and pH on the binding of genomic DNA to Organon Teknika Silica.
FIG. 5(b) shows the effects of various salts and pH on the binding of genomic DNA to Sigma Diatomaceous Earth.
FIG. 5(c) shows the effects of various salts and pH on the binding of genomic DNA to Bio101 Glassmilk.
FIG. 5(d) shows the effects of pH on the binding of genomic DNA to various solid phases in the presence of NaCl.
FIG. 5(e) shows the effects of pH on the binding of genomic DNA to various solid phases in the presence of GuSCN.
FIG. 5(f) shows the effects of pH on the binding of genomic DNA to Organon Teknika Silica in the presence of NaBr.
FIG. 5(g) shows the effects of pH on the binding of genomic DNA to various solid phasess in the presence of NaI.
FIG. 5(h) shows the effects of pH on the binding of genomic DNA to various solid phases in the presence of NaCl (results are shown as relative efficiencies at different pH levels normalized to the recovery at pH 6).
FIG. 5(i) shows the effects of pH on the binding of genomic DNA to various solid phases in the presence of GuSCN (results are shown as relative efficiencies at different pH levels normalized to the recovery at pH 6).
FIG. 5(j) shows the effects of pH on the binding of genomic DNA to Organon Teknika Silica in the presence of NaBr (results are shown as relative efficiencies at different pH levels normalized to the recovery at pH 6).
FIG. 5(k) shows the effects of pH on the binding of genomic DNA to various substrates in the presence of NaI, results are shown as relative efficiencies at different pH levels normalized to the recovery at pH 6.
Figure 5B:
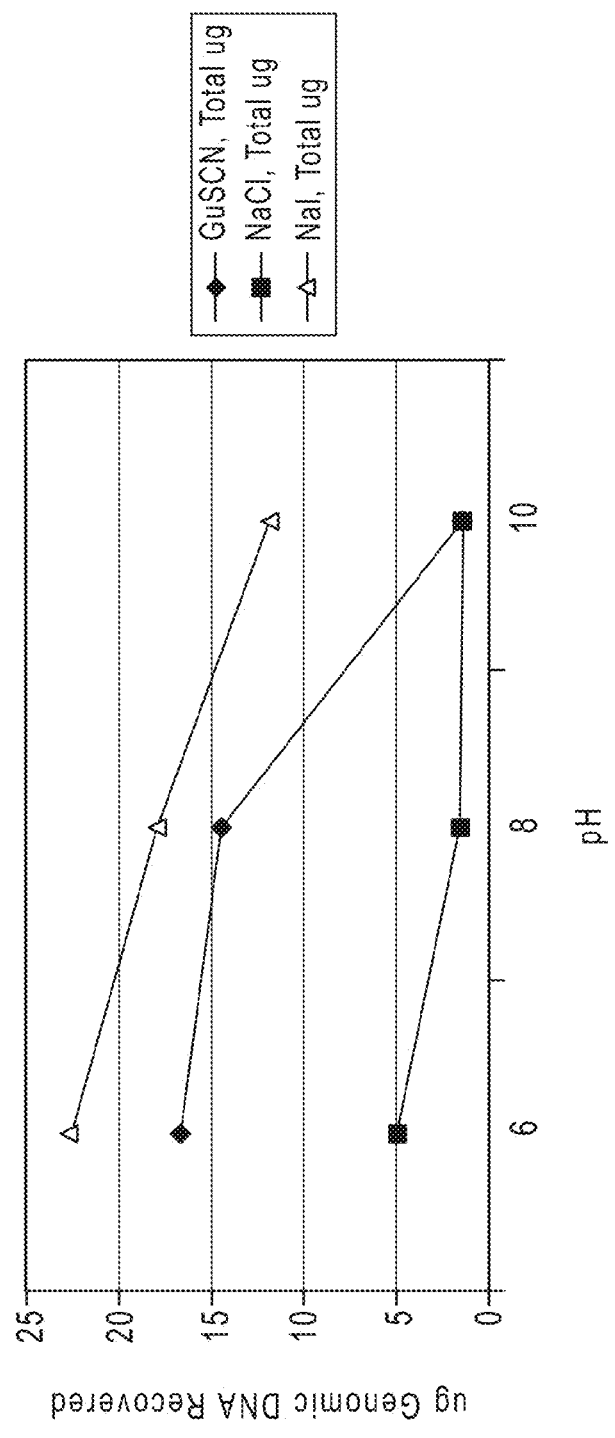
Figure 5C:
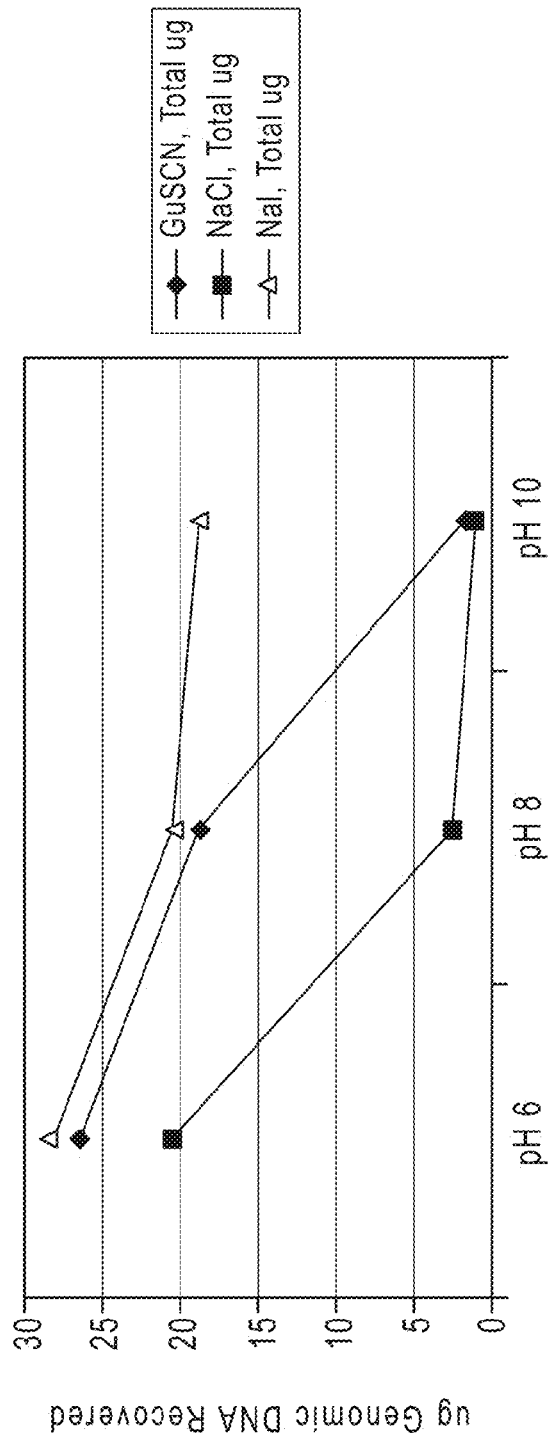
Figure 5D:
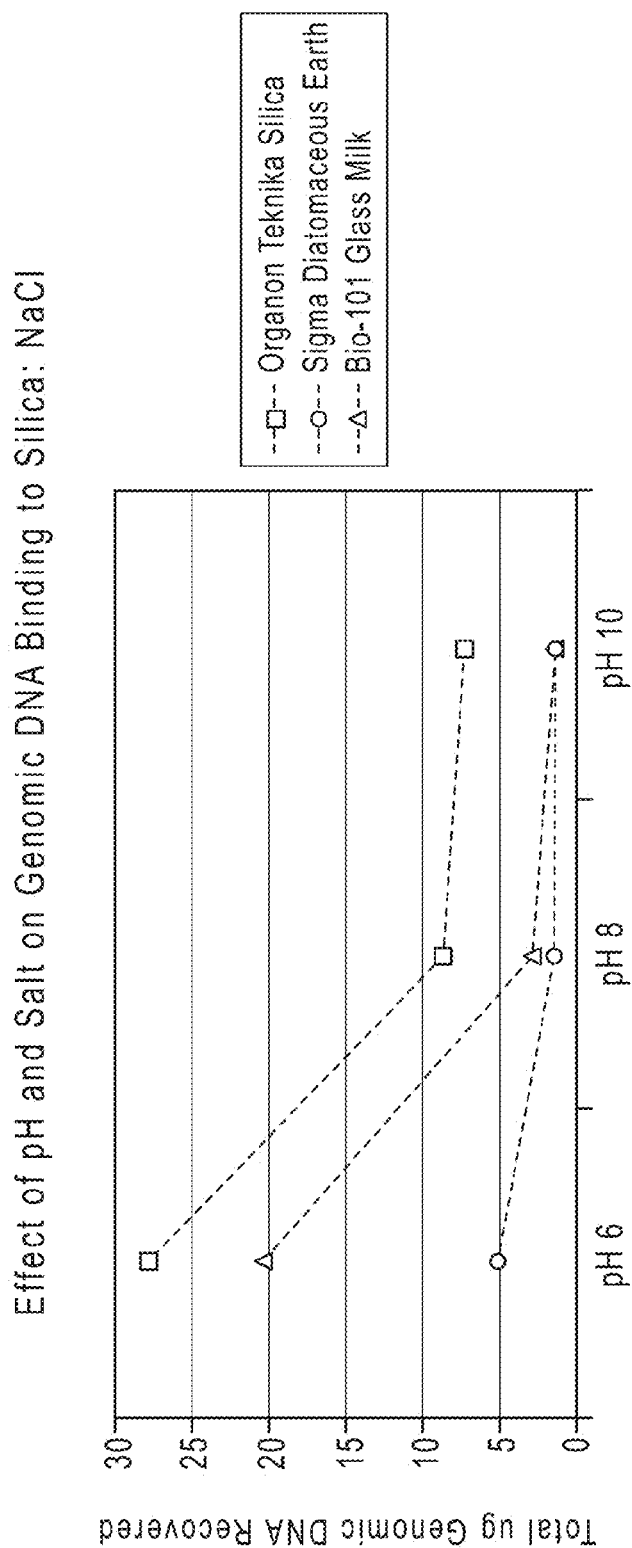
Figure 5E:
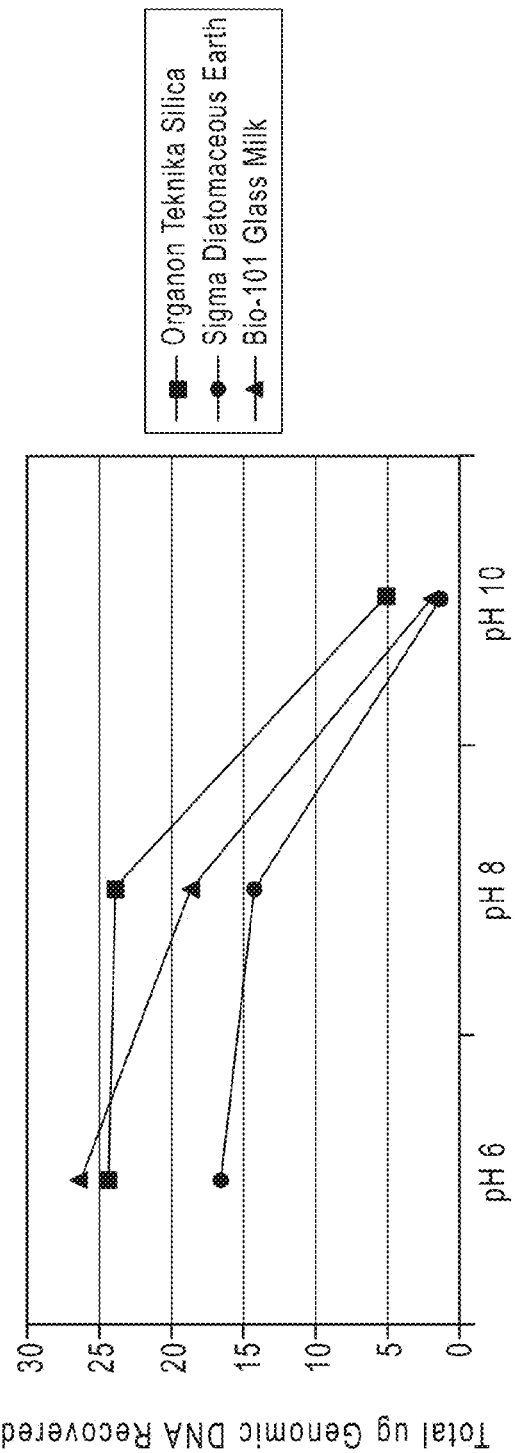
Figure 5F:
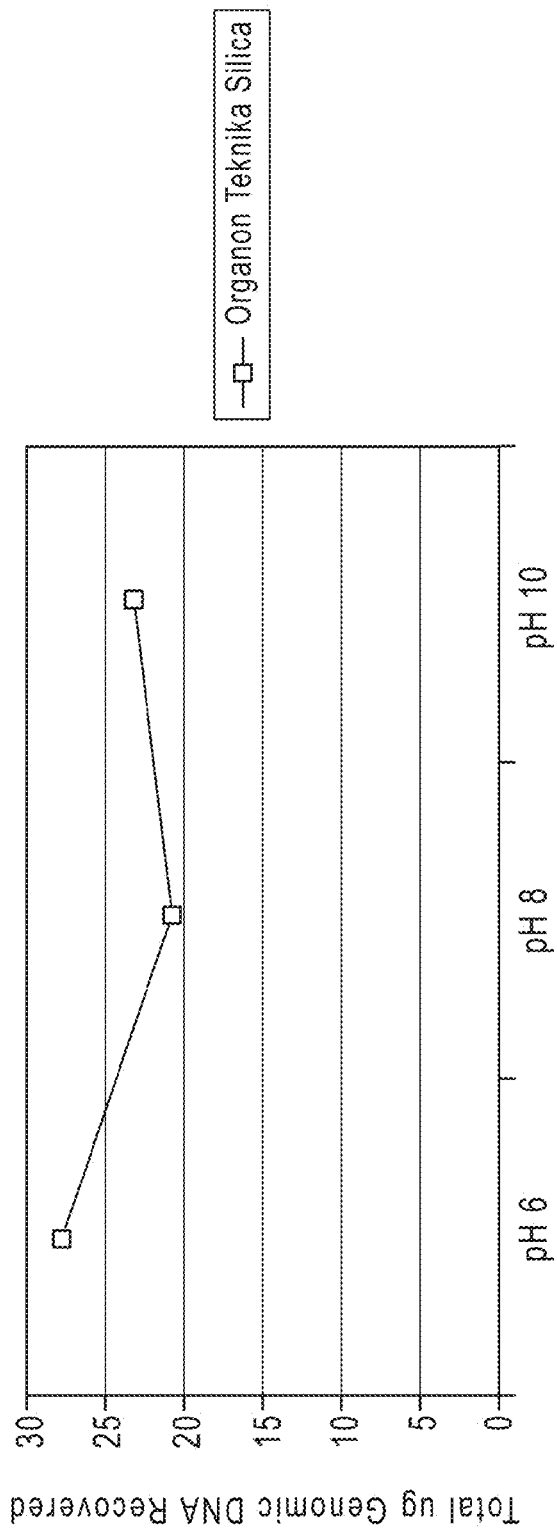
Figure 5G:
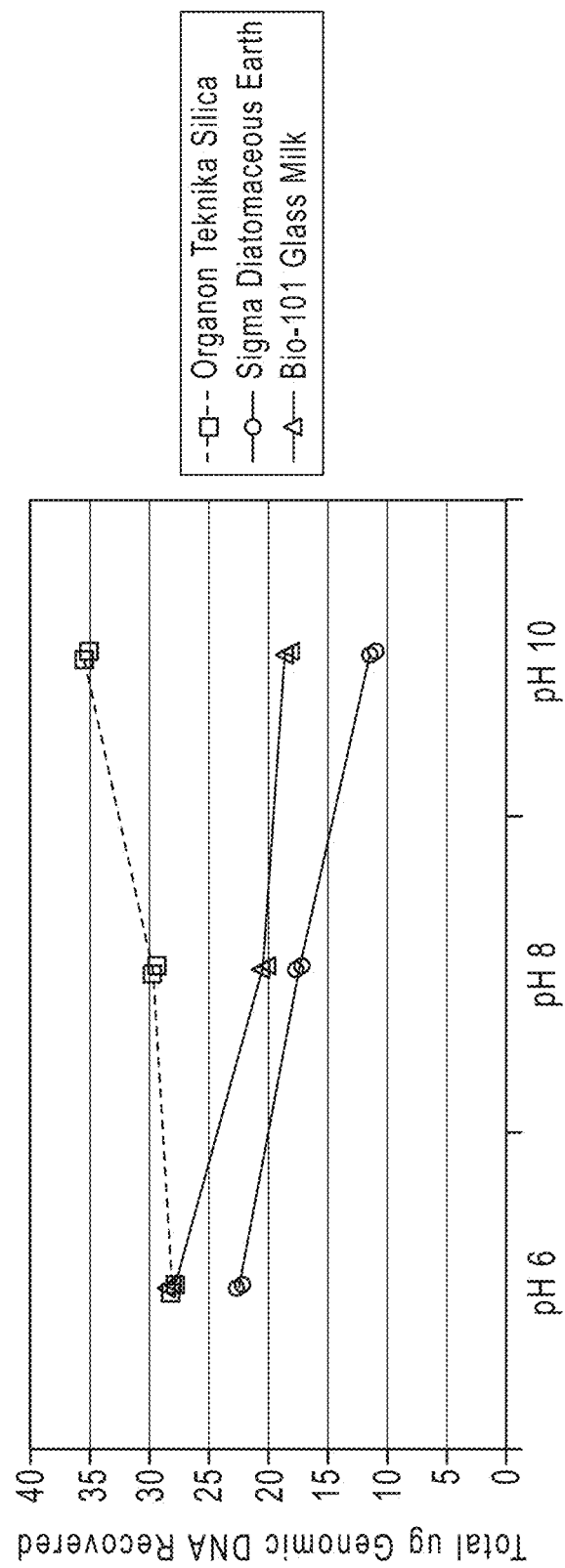
Figure 5H:
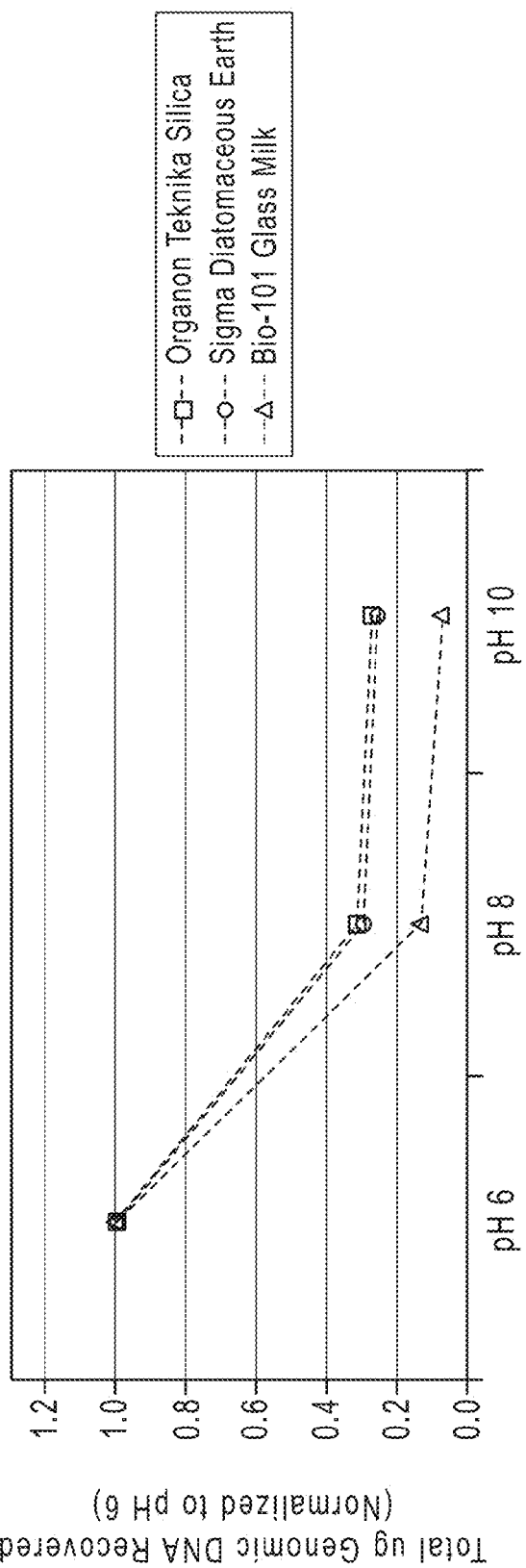
Figure 5I:
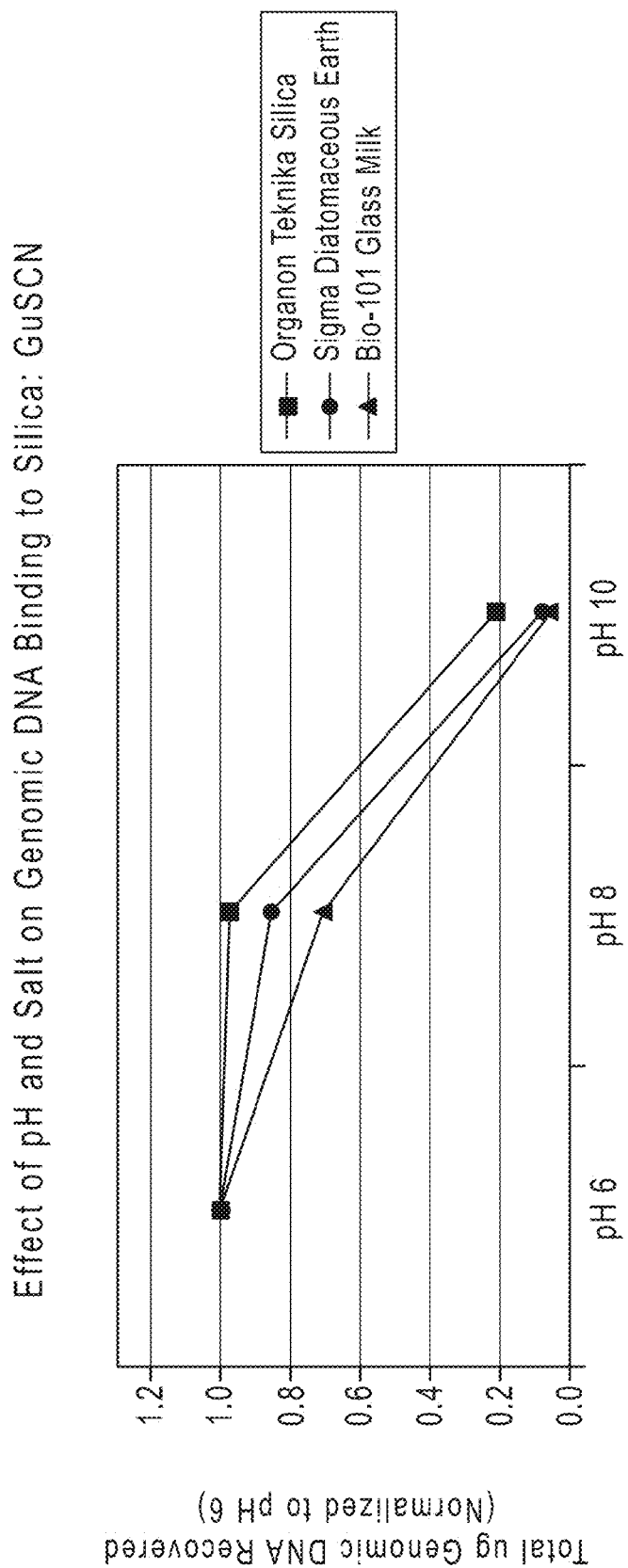
Figure 5J:
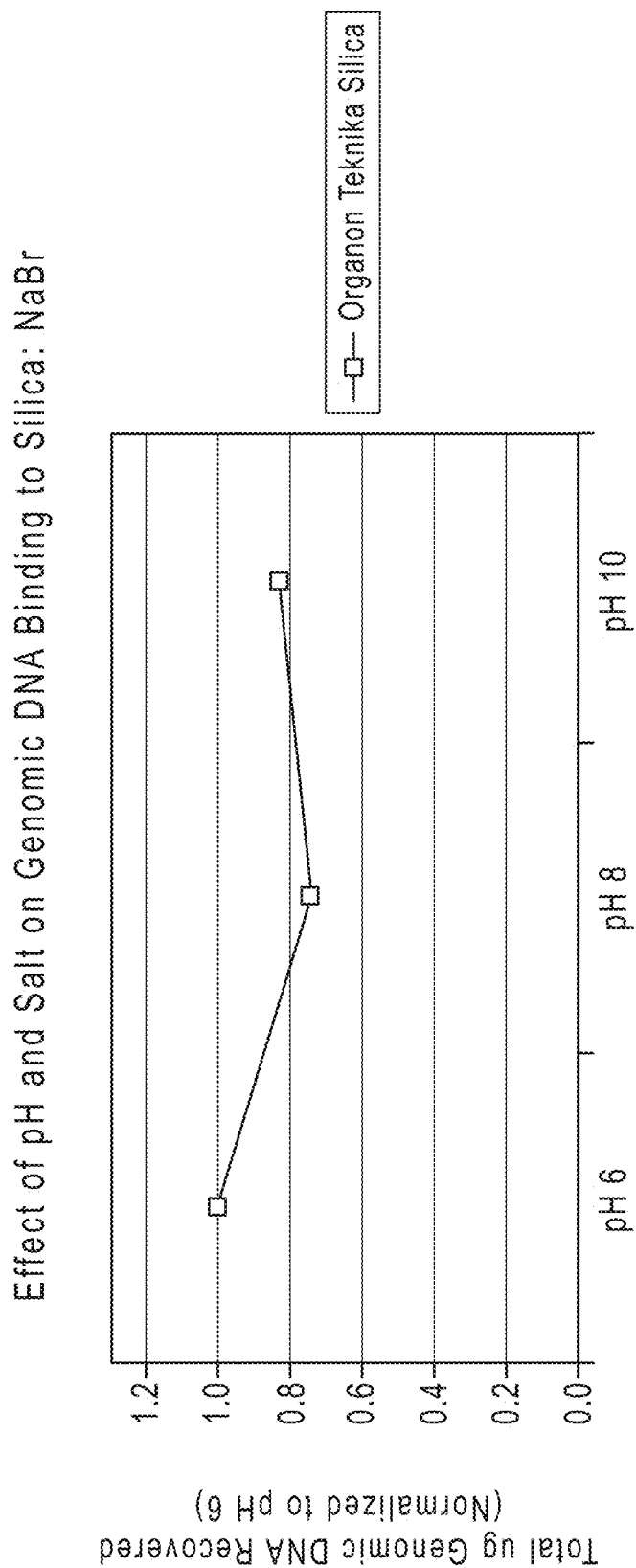
Figure 5K:
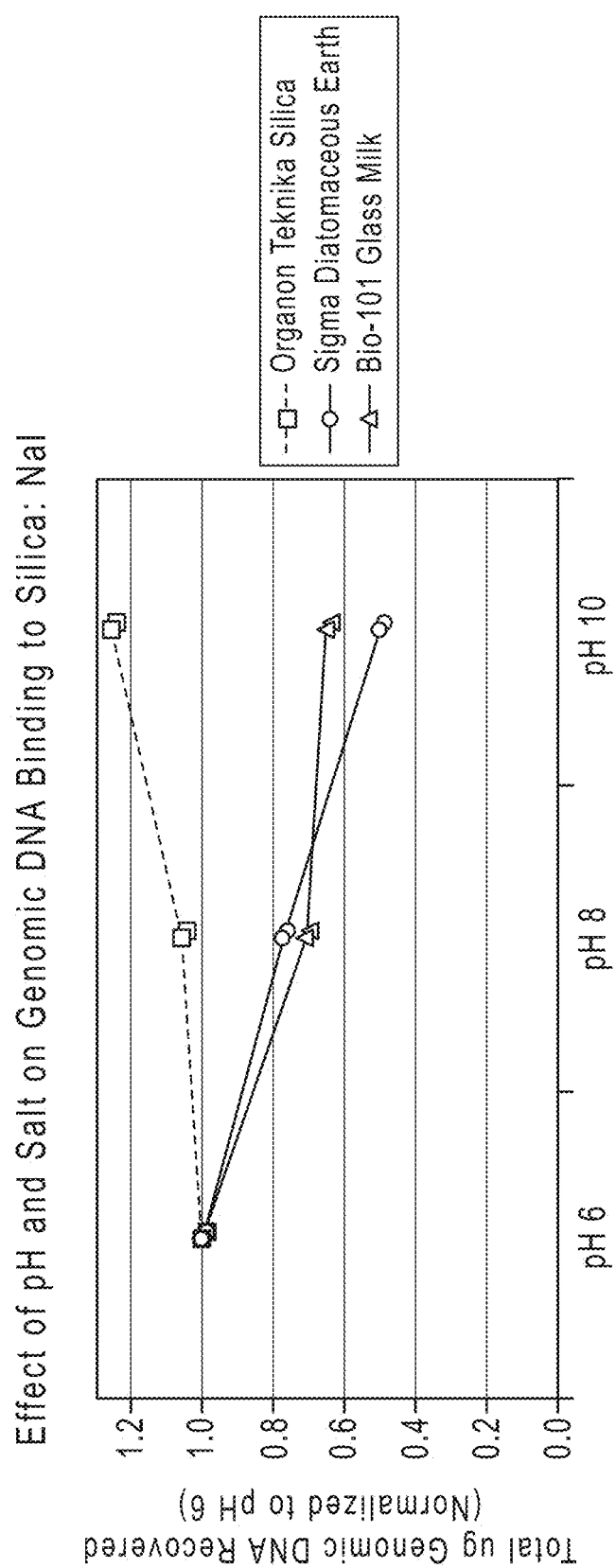

When binding at pH 8, many of the matrices showed a moderately higher binding of DNA as compared to RNA. Selectivity for DNA binding was increased with sodium iodide (see FIG. 4).

Example 4

In order to investigate the relationship between DNA binding to solid-phases, DNA was bound to several solid-phases using buffers with different salt compositions and pH levels.

The following solid phases used in this study were prepared as described in Example 1: Silica, Diatomaceous Earth, and Glassmilk Spin Buffer #4. For these studies, sheared calf thymus DNA prepared as described in Example 1 was used as the source of genomic DNA.

Each solid phase and buffer combination was assayed once. Sheared calf thymus DNA (25 .mu.g-50 .mu.l at 0.5 mg/ml) was added to different 1.5 ml microcentrifuge tubes containing 0.45 ml of one of the following buffers: (1) 50 mM MES, pH 6, 4.75 M guanidine thiocyanate; (2) 50 mM MES, pH 6.0, 4.75 M sodium chloride; (3) 50 mM MES, pH 6.0, 4.75 M sodium bromide; (4) 50 mM MES, pH 6.0, 4.75 M sodium iodide; (5) 50 mM Tris-HCl, pH 8, 4.75 M guanidine thiocyanate; (6) 50 mM Tris-HCl, pH 8, 4.75 M sodium chloride; (7) 50 mM Tris-HCl, pH 8, 4.75M sodium bromide; (8) 50 mM Tris-HCl, pH 8, 4.75 M sodium iodide; (9) 50 mM AMP, pH 10, 4.75M guanidine thiocyanate; (10) 50 mM AMP, pH 10, 4.75 M sodium chloride; (11) 50 mM AMP, pH 10, 4.75 M sodium bromide; or (12) 50 mM AMP, pH 10, 4.75 M sodium iodide.

Nucleic acid was incubated for 5 to 10 minutes at ambient temperature in the buffered solution, sometimes with occasional mixing. Each of the three solid phases (10 mg) was added separately to each of the buffered nucleic acid solutions. Those mixtures were incubated for 10 minutes at ambient temperature with occasional mixing. following the binding incubation, the particles were centrifuged (4000.times.g, 1 minute) and washed twice with 0.5 ml of the binding buffer that had been used for the binding incubation. The particles were then washed three times with 0.5 ml of 70% ethanol.

Following the last ethanol wash, the particles were allowed to air dry at ambient temperature for 5-10 minutes. The bound nucleic acid was first eluted with 0.25 ml of 50 mM Tris, pH 9 for 5 minutes at 56.degree. C. with constant mixing, and the eluted nucleic acid was collected. Any residual nucleic acid bound to the particles was eluted with 0.25 ml of 0.1 N NaOH at 56.degree. C. for 5 minutes with constant mixing and the eluted nucleic acid was collected. The amount of nucleic acid was quantified by spectrophotometry. Results for each set of experiments are shown in FIGS. 5(a)-(k).

Previous investigators showed that DNA binding to silica decreases as the pH of the buffer is increased above 7 (Melzak, Kathryn A. et al. (1996), Driving Forces for DNA Adsorption to Silica in Perchlorate Solutions, Journal of Colloid and Interface Science 181: 635-644). The results in this example showed that the salt composition influenced the effect of pH on DNA binding. The results also demonstrated that source of the solid phase altered the magnitude of the effect of the salt and the absolute amount of nucleic acid that was bound. The effect of salt on pH sensitivity of DNA binding shows the following order of sensitivity to pH:NaCl>GuSCN>NaBr>NaI Example 5

The effect of pH and particular salts on RNA binding was also evaluated. The solid phases Binding Matrix and Glassmilk particles were prepared as described in Example 1. Rat liver total RNA was the source of RNA.

Each solid phase and buffer combination was assayed once. Rat liver total RNA (15 .mu.g of RNA, 6 .mu.l of a 2.5 mg/ml concentration) was added to 1.5 ml microcentrifuge tubes containing 0.45 ml of one of the following buffers: (1) 50 mM Tris-HCl, pH 8, 4.75 M guanidine thiocyanate; (2) 50 mM Tris-HCl, pH 8, 4.75 M sodium chloride; (3) 50 mM Tris-HCl, pH 8, 4.75 M sodium iodide; (4) 50 mM MES, pH 6, 4.75 M guanidine thiocyanate; (5) 50 mM MES, pH 6, 4.75 M sodium iodide; (6) 50 mM MES, pH 6, 4.75 M sodium chloride; (7) 50 mM AMP, pH 10, 4.75 M guanidine thiocyanate; (8) 50 mM AMP, pH 10, 4.75 M sodium iodide; or (9) 50 mM AMP, pH 10, 4.75 M sodium chloride. Nucleic acid was incubated up to 5 minutes at ambient temperature in the buffered solution, with occasional mixing. Each of the two solid phases (10-187 mg) was added separately to the buffered nucleic acid solutions. Those mixtures were incubated 10 minutes at ambient temperature with occasional mixing. Following the binding incubation, the particles were centrifuged (15,800.times.g, 1 minute) and washed twice with 0.5 ml of the binding buffer that had been used for the binding incubation. Subsequently, the particles were washed two or four times with 0.5 ml of 70% ethanol. The particles which were washed twice with ethanol were then washed once with 0.5 ml of acetone and were allowed to dry for 5 minutes at 56.degree. C. The bound nucleic acid was first eluted with 0.25 ml or 0.275 ml of 10 mM Tris, pH 9 for 5 minutes at 56.degree. C. with constant mixing, and the eluted nucleic acid was collected. Any residual nucleic acid bound to the particles was subsequently eluted with 0.25 or 0.275 ml of 0.1 N NaOH for 5 minutes with constant mixing and the eluted nucleic acid was collected. The amount of nucleic acid was quantified by spectrophotometry.

Figure 6:
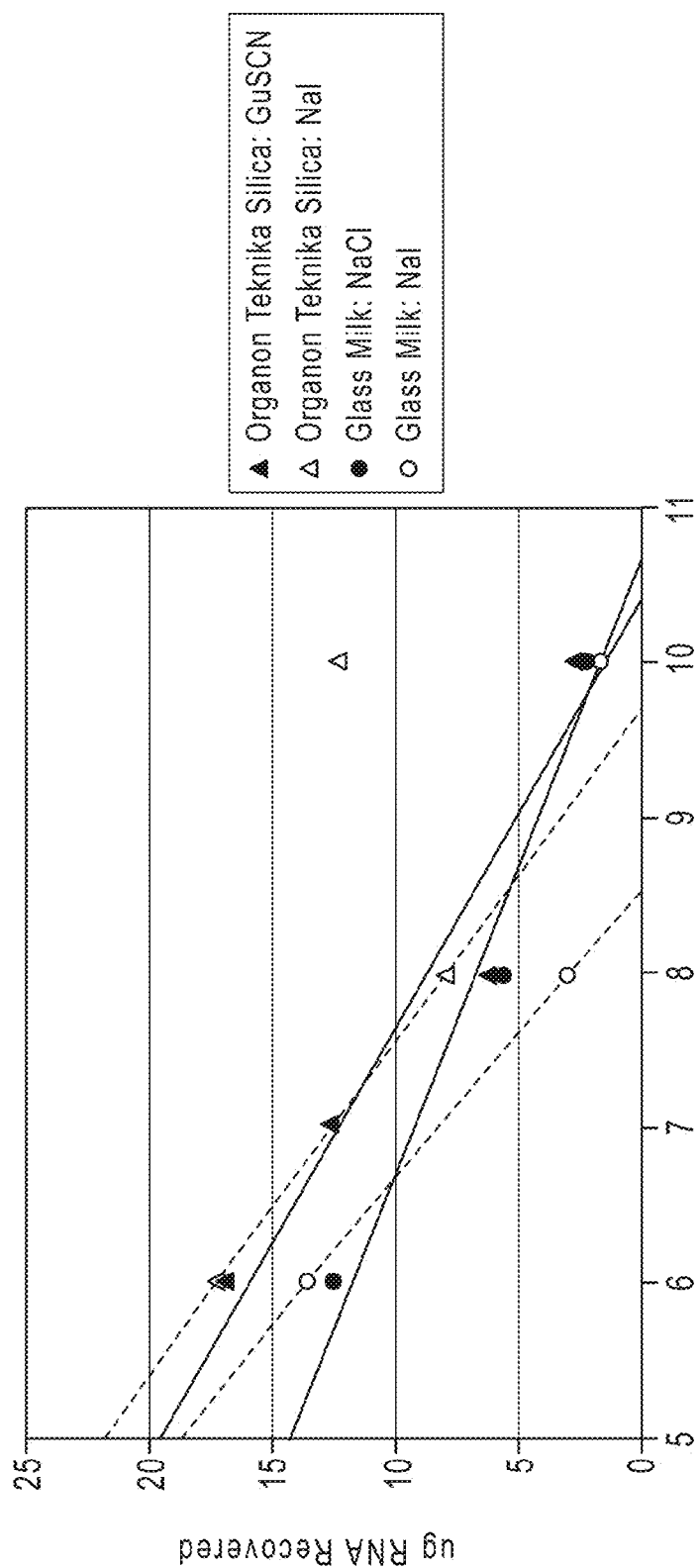
FIG. 6 shows the effects of pH and salt on the binding of RNA to either Organon Teknika Silica or to Glassmilk.

The results are shown in FIG. 6. RNA binding to the two solid-phases evaluated showed a large dependency on pH. There was a significant reduction in RNA binding with all salts when the pH of the buffer was increased.

Example 6

The selectivity of Glass Milk was evaluated further as a function of pH and ionic composition during binding. Glassmilk Spin Buffer #4 was prepared as described in Example 1. Sheared calf thymus DNA was prepared as described in Example 1. Rat liver total RNA was the source of RNA.

Each nucleic acid and buffer combination was assayed once. Either 25 .mu.g (50 .mu.l of a 0.5 mg/ml solution in water) of sheared calf thymus DNA or 15 .mu.g (6 .mu.l of a 2.5 mg/ml solution in water) of rat liver total RNA was added separately to separate 1.5 ml microcentrifuge tubes containing 0.45 ml of one of the following buffers: (1) 50 mM MES, pH 6.0, 4.75 M sodium chloride; (2) 50 mM MES, pH 6.0, 4.75 M sodium iodide; (3) 50 mM Tris-HCl, pH 8, 4.75 M sodium chloride; (4) 50 mM Tris-HCl, pH 8, 4.75 M sodium iodide; (5) 50 mM AMP, pH 10, 4.75 M sodium iodide; or (6) 50 mM AMP, pH 10, 4.75 M sodium chloride. Thus, there were 12 separate containers with each combination of the DNA or RNA and individual buffers. The solid phase (186 mg) was added to the buffered nucleic acid solutions and the mixtures were incubated 10 minutes at ambient temperature with occasional mixing. Following the binding incubation, the particles were centrifuged (15,800.times.g, 1 minute) and washed twice with 0.5 ml of the binding buffer that had been used for the binding incubation. Subsequently, the particles were washed four times with 0.5 ml of 70% ethanol. The bound nucleic acid was first eluted with 0.25 ml of 10 mM Tris, pH 9 for 5 minutes at 56.degree. C. with constant mixing and the eluted nucleic acid was collected. Any residual nucleic acid bound to the particles was eluted with 0.25 of 0.1 N NaOH for 5 minutes with constant mixing and the eluted nucleic acid was collected. The amount of nucleic acid was quantified by spectrophotometry.

Figure 7:
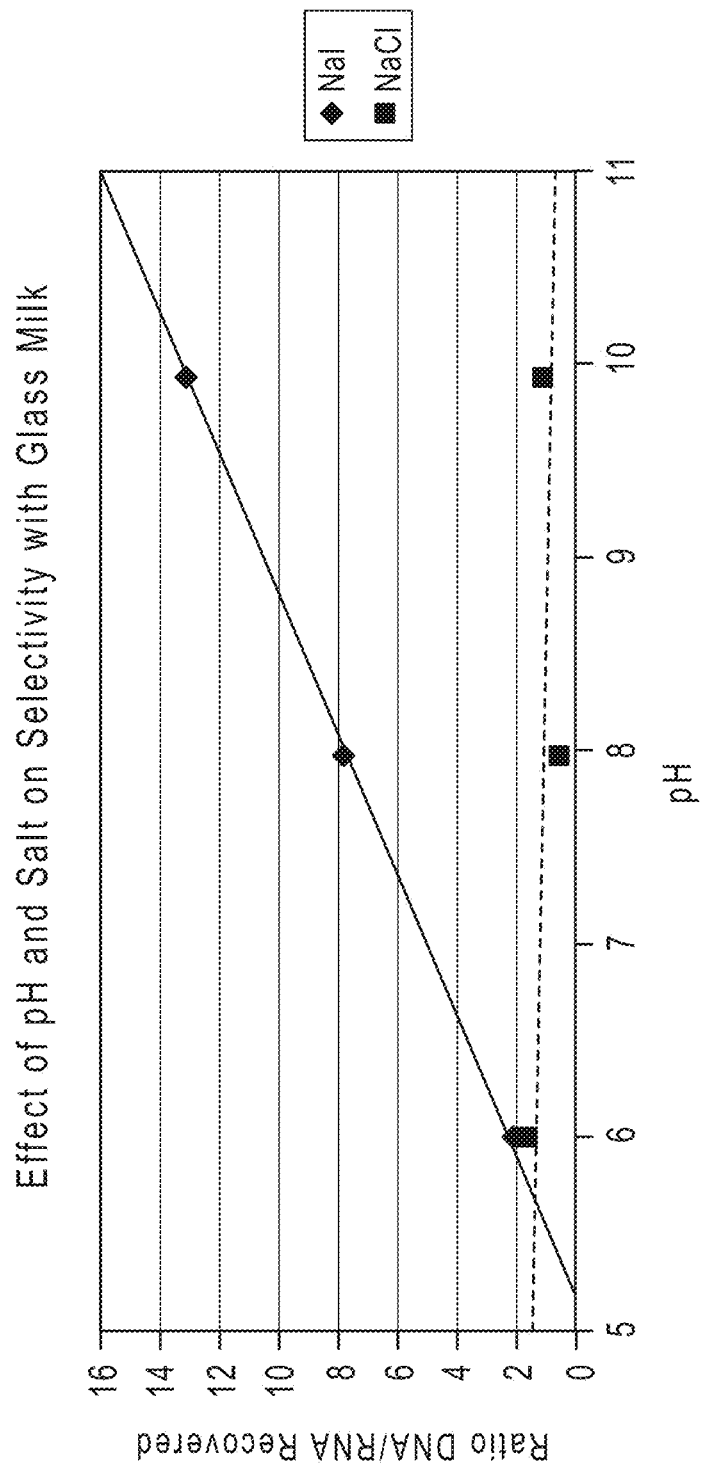
FIG. 7 shows the effects of salt and pH on the selectivity of nucleic acid binding to Glassmilk in the presence of either NaI or NaCl.

The results are shown in FIG. 7. With sodium iodide as the binding salt, selectivity for DNA binding increased when the pH was increased. In contrast, binding in the presence of sodium chloride did not show increased specificity at an alkaline pH.

Example 7

The effect of pH on DNA and RNA binding in the presence of sodium iodide was evaluated with several solid phases. Silicon dioxide (Sigma, Product Number S-5631, Lot 58H0154), Davisil Grade 643 Silica Gel (Spectrum, Product Number Sil 66, Lot NE 0387) and Uniform Silica Microspheres (Bangs Laboratories, Inc. Catalog Code SS05N, Inv # L0002188) were used for the following study. Prior to use, the silicon dioxide and Davisil Grade Silica Gel particles were prepared as follows. The particles were washed once with water, once with 500 mM ammonium bifluoride, once with 100 mM nitric acid, twice with 100 mM ammonium hydroxide, twice with 300 mM ammonium hydroxide, once with ethanol, and nine times with water. All particles of the three solid phases were prepared and stored as a 200 mg/ml (20%) slurry in water.

Total rat liver RNA was the source of RNA. For genomic DNA, sheared calf thymus DNA was prepared as described in Example 1.

Each solid phase, nucleic acid, and buffer combination was performed in triplicate. Either sheared calf thymus DNA (30 .mu.g, addition of 50 .mu.L of a 590 .mu.g/mL stock) or total rat liver RNA (30 .mu.g, addition of 50 .mu.L of a 600 .mu.g/mL stock) was added separately to separate 1.5 ml microcentrifuge tubes containing 50 .mu.L of silica particles (10 mg) along with 0.45 ml of one of the following buffers: (1) 50 mM MES, pH 6.0, 4.8 M NaI; (2) 50 mM Hepes, pH 7.0, 4.8 M NaI; (3) 50 mM Tris, pH 8, 4.8 M NaI; (4) 50 mM Tris, pH 9, 4.8 M NaI; or (5) 50 mM AMP, pH 10, 4.8 M NaI. For each of the three solid phases, binding of either DNA or RNA was evaluated with each of the five buffers in triplicate, resulting in a total of thirty containers per solid phase. Nucleic acid was incubated 5-30 minutes at ambient temperature in the buffered solution, with continuous mixing using a Vortex Genie-2 mixer at setting 7 (Scientific Industries).

Following binding, the particles were centrifuged 14,000 rpm for 1 minute and the supernatant removed. The particles were subsequently washed four times with 1 mL of 70% ethanol. Following addition of 250 .mu.L of 50 mM Tris, pH 9.0, the particles were incubated for 5-6 minutes at 56.degree. C. with continuous shaking (1400 rpm) on an Eppendorf Thermomixer R. The particles were centrifuged at 14,000 rpm for 1 minute and the supernatant containing eluted nucleic acid was collected. In order to detect the presence of residual bound nucleic acid, 250 .mu.L of 100 mM NaOH was added, the particles were incubated for 5-70 minutes at 56.degree. C. with continuous shaking (1400 rpm) on an Eppendorf Thermomixer R, and the eluted nucleic acid was collected. The amount of nucleic acid in each fraction was quantified spectrophotometrically.

Figure 8A:
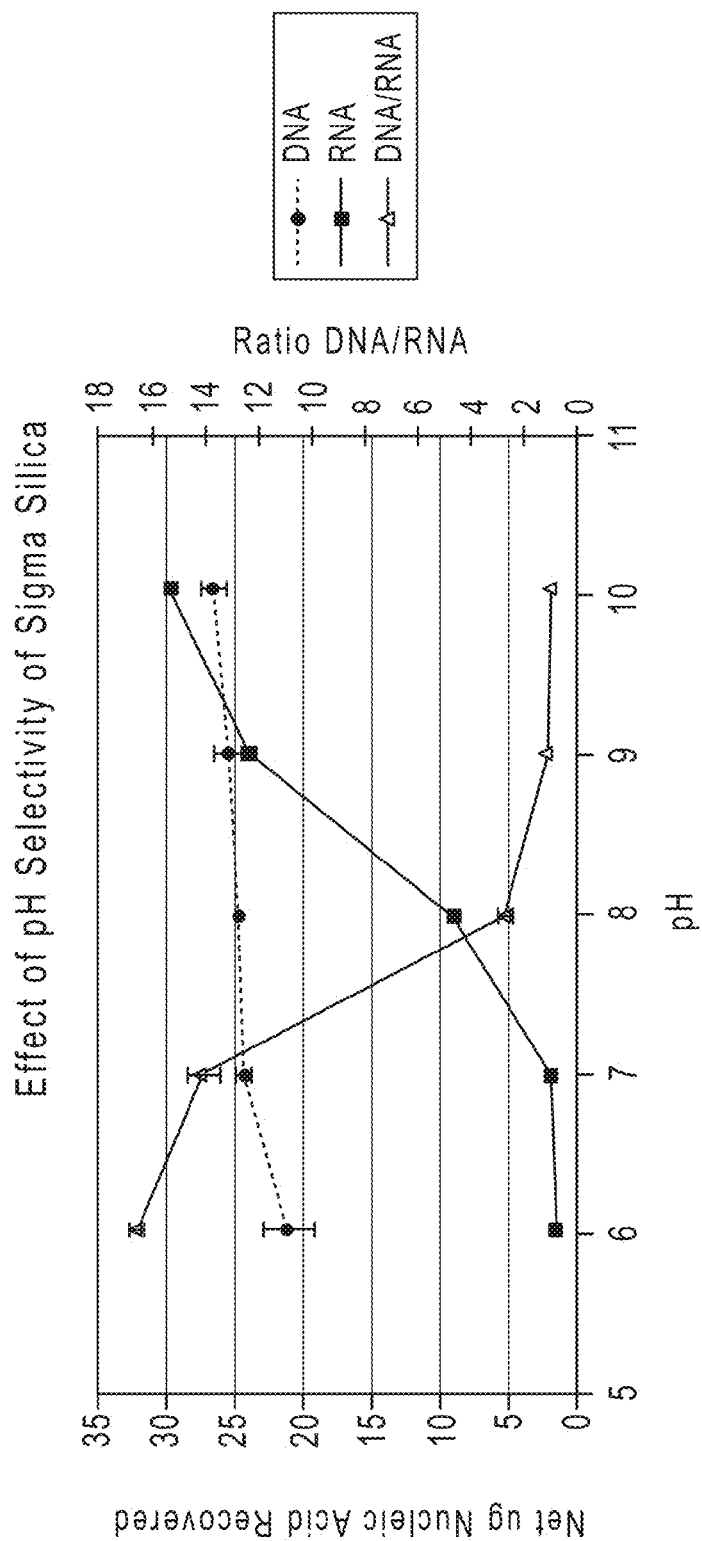
FIG. 8(a) shows the effects of pH on the selectivity of binding of nucleic acid (both RNA and DNA) to Sigma Silica. Binding was performed in 4.8 M NaI using each of the following buffers: 50 mM MES, pH 6.0; 50 mM HEPES, pH 7.0; 50 mM Tris, pH 8.0; 50 mM Tris, pH 9.0; or 50 mM AMP, pH 10.0.
Figure 8B:
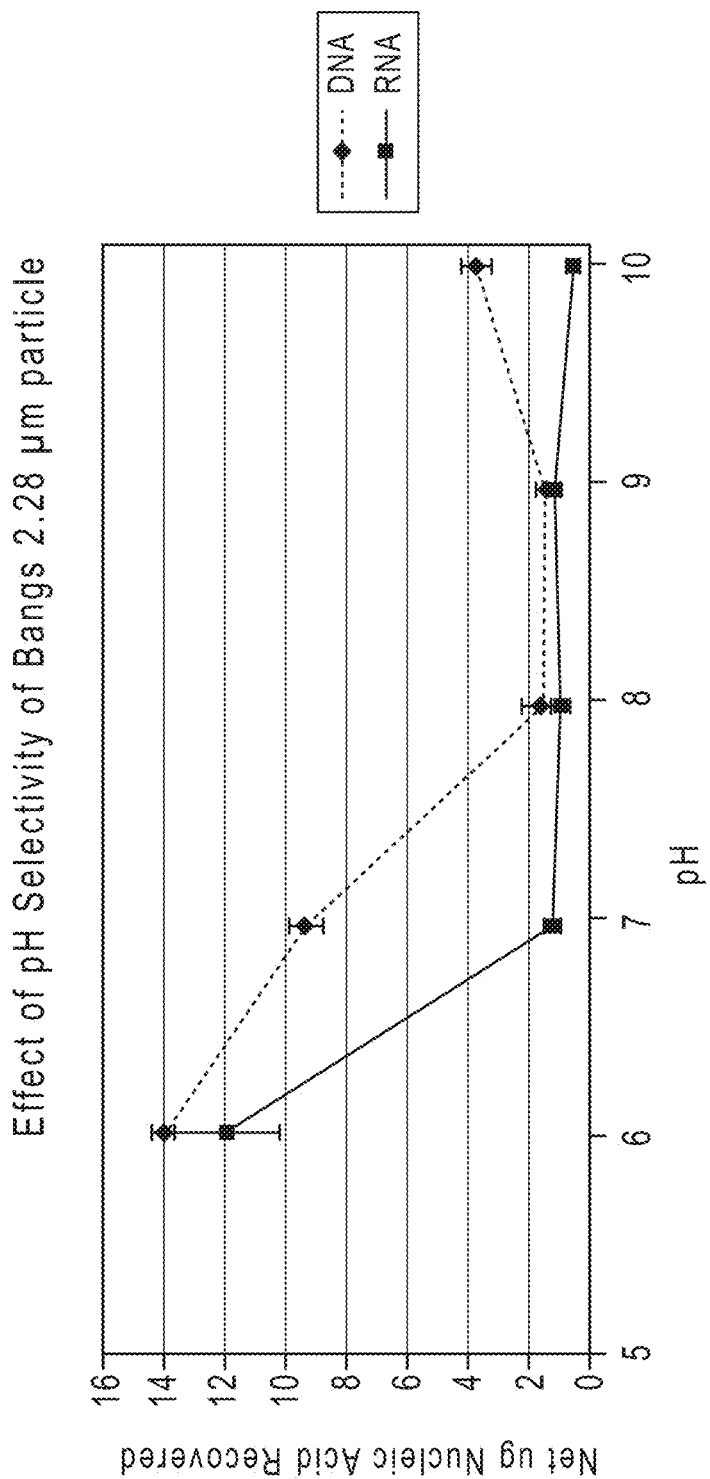
FIG. 8(b) shows the effects of pH on the selectivity of binding of nucleic acid (both RNA and DNA) to Bangs 2.28 .mu.m particles. Binding was performed in 4.8 M NaI using each the following buffers: 50 mM MES, pH 6.0; 50 mM HEPES, pH 7.0; 50 mM Tris, pH 8.0; 50 mM Tris, pH 9.0; or 50 mM AMP, pH 10.0.
Figure 8C:
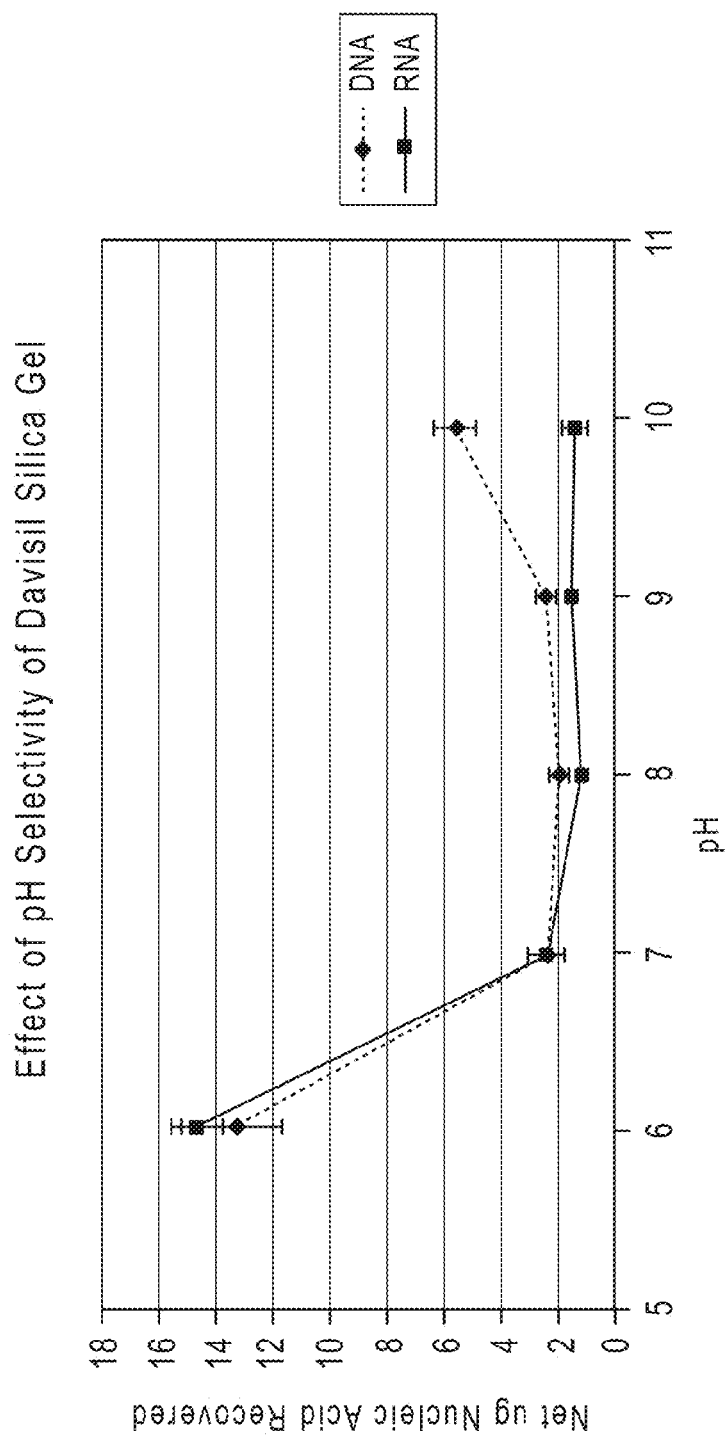
FIG. 8(c) shows the effects of pH on the selectivity of binding of nucleic acid (both RNA and DNA) to Davisil Silica Gel. Binding was performed in 4.8 M NaI using each of the following buffers: 50 mM MES, pH 6.0; 50 mM HEPES, pH 7.0; 50 mM Tris, pH 8.0; 50 mM Tris, pH 9.0; or 50 mM AMP, pH 10.0.

The results are shown in FIGS. 8(a)-(c). Almost all siliceous solid phases that were examined showed an increased selectivity for DNA binding at alkaline pH when sodium iodide was the binding salt. DNA binding to Sigma Silica in the presence of sodium iodide was relatively insensitive to pH. In contrast, increasing the pH resulted in a dramatic decrease in binding of RNA to the same solid phase. Thus, DNA selectivity was seen at an alkaline pH in the presence of NaI.

Example 8

The effect of pH on DNA selectivity was examined using several solid phases when sodium iodide was the binding salt. Silica (Organon Teknika), Diatomaceous Earth, silicon dioxide (Sigma Silica), Binding Matrix, and Glassmilk were prepared as described in Example 1. Binding was carried out in the presence of sheared calf thymus DNA (as described in Example 1) or rat liver total RNA. Binding was performed in the following binding buffers: (1) 50 mM Tris-HCl, pH 8, 4.75 M NaI; or (2) 50 mM AMP, pH 10, 4.75 M NaI.

Each solid phase, nucleic acid, and buffer combination was assayed one to three times. Either sheared calf thymus DNA (25 .mu.g) or total rat liver RNA (15-25 .mu.g) was added to separate 1.5 ml microcentrifuge tubes containing 4.5 ml of one of the following buffers: (1) 50 mM Tris-HCl, pH 8, 4.75 M NaI; or (2) 50 mM AMP, pH 10, 4.75 M NaI.

Each of the five solid phases (10-186 mg) was added separately to the combinations of RNA or DNA and the individual buffers. The data in FIG. 9 reflects for each of the RNA and DNA experiments: (1) three separate containers with Glassmilk at pH 8 and 2 containers with Glassmilk at pH 10; (2) two separate containers with Binding Matrix at pH 8 and 1 container with Binding Matrix at pH 10; (3) one separate container with Sigma Silica at pH 8 and 1 container with Sigma Silica at pH 10; (4) one separate container with Silica (Organon Teknika) at pH 8; and (5) two separate containers with Diatomaceous Earth at pH 8 and 1 container with Diatomaceous Earth at pH 10. Thus, there were 14 different containers with each of the possible combinations of solid phase and buffer for the RNA, and there were 14 different containers with each of the possible combinations of solid phase and buffer for the DNA. The mixtures were incubated for 10 minutes at ambient temperature with occasional mixing. Following the binding incubation, the particles were centrifuged (15,800.times.g, 1 minute) and washed twice with 0.5 ml of the binding buffer that had been used in the binding incubation. Subsequently, the particles were washed three to four times in 0.5 ml of 70% ethanol.

Following the last ethanol wash, particles were allowed to air dry at ambient temperature or at 56.degree. C. for 5-10 minutes. The bound nucleic acid was first eluted with 0.25 ml of 10 mM Tris, pH 9 for 5 minutes at 56.degree. C. with constant mixing and the eluted nucleic acid was collected. Any residual nucleic acid bound to the particles was eluted with 0.25 ml of 0.1 N NaOH at 56.degree. C. for 5 minutes with constant mixing and the eluted nucleic acid was collected. The amount of nucleic acid was quantified by spectrophotometry.

Figure 9:
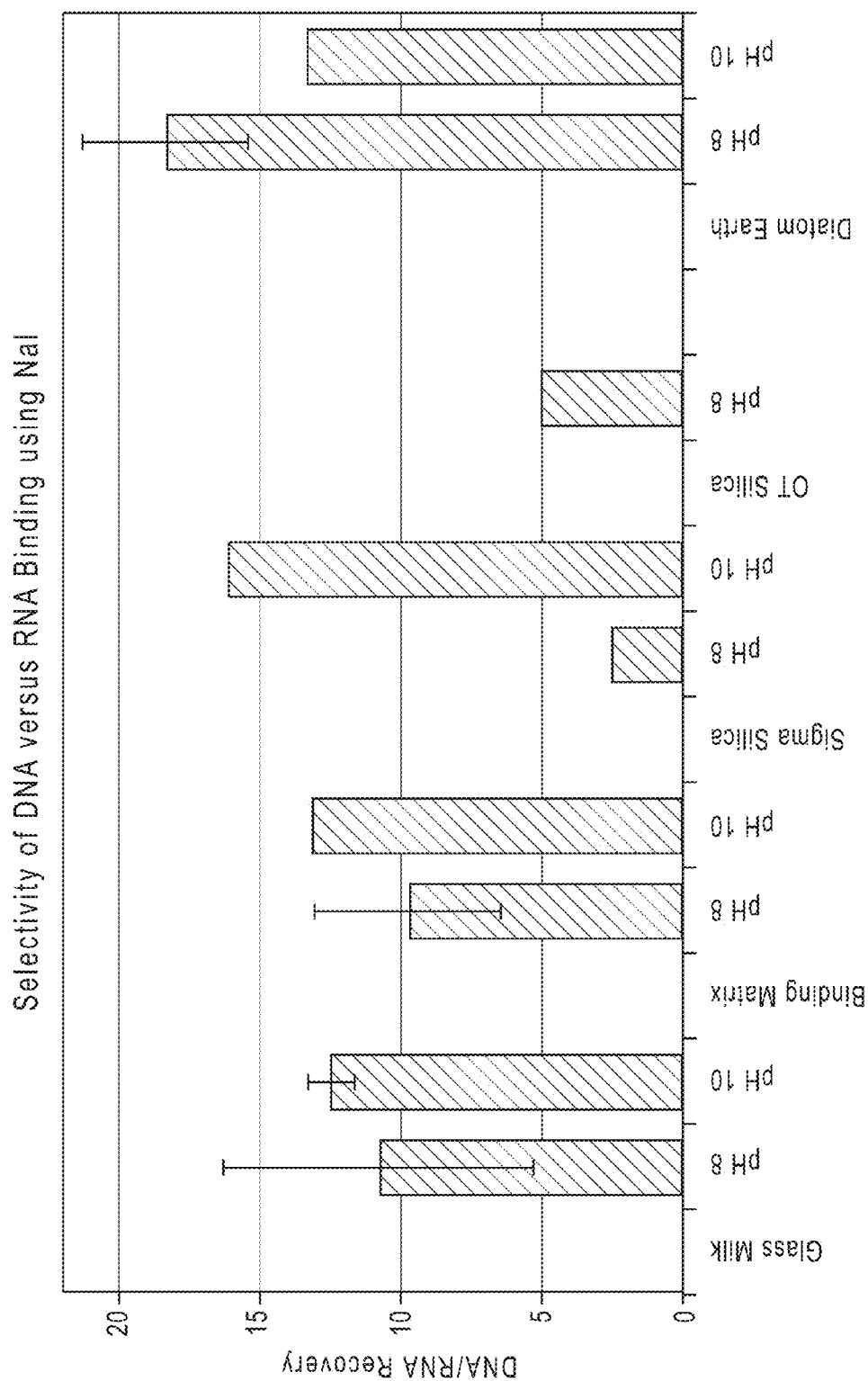
FIG. 9 shows the selectivity of DNA versus RNA binding of various solid phases in the presence of NaI at either pH 8 or pH 10.

The results are shown in FIG. 9. Each of the solid phases that were examined showed a greater specificity for DNA binding at the alkaline pH. There appeared to be a reduced affinity for RNA at alkaline pH. Binding of DNA at concentrations below saturation of the solid phase was efficient. Virtually all of the added DNA was bound and recovered from the siliceous solid phase. In contrast, binding of RNA under these conditions was inefficient even when the amount added was high.

Example 9

To measure the difference between the binding of DNA and RNA to silicon dioxide, and the level of saturation, the following experiment was performed. The solid phase examined was silicon dioxide, which was prepared as described in Example 1. The nucleic acids studied were sheared calf thymus DNA (prepared as described in Example 1) and total rat liver RNA.

Sheared calf thymus DNA (126 .mu.g, 60 .mu.g, 30 .mu.g, 15 .mu.g, or 5 .mu.g) or total rat liver RNA (125 .mu.g, 60 .mu.g, 30 .mu.g, 15 .mu.g, or 5 .mu.g) was added in 50 .mu.L to separate Eppendorf tubes (1.5 ml) containing 450 .mu.l of binding buffer (50 mM Tris, pH 8, 4.8 M sodium iodide), and 10 mg of Sigma silicon dioxide particles (Sigma, prepared as described in Example 7). The work was performed in triplicate, so there were 15 containers for the five different amounts of DNA and 15 containers for the five different amounts of RNA. The samples were incubated at ambient temperature for 5-10 minutes on a Vortex Genie-2 mixer at setting 7 (Scientific Industries).

Following binding, the particles were centrifuged 14,000 rpm for 1 minute and the supernatant was removed. The particles were subsequently washed four times with 1 ml of 70% ethanol. Following addition of 250 .mu.L of 50 mM Tris, pH 9.0, the particles were incubated for 5-10 minutes at 56.degree. C. with continuous shaking (1400 rpm) on an Eppendorf Thermomixer R. The particles were centrifuged at 14,000 rpm for 1 minute and the supernatant containing eluted nucleic acid was collected. In order to detect the presence of residual bound nucleic acid, 250 .mu.L of 100 mM NaOH was added, the particles were incubated for 5-10 minutes at 56.degree. C. with continuous shaking (1400 rpm) on an Eppendorf Thermomixer R, and the eluted nucleic acid was collected. The amount of nucleic acid in each fraction was quantitated spectrophotometrically.

Figure 10:
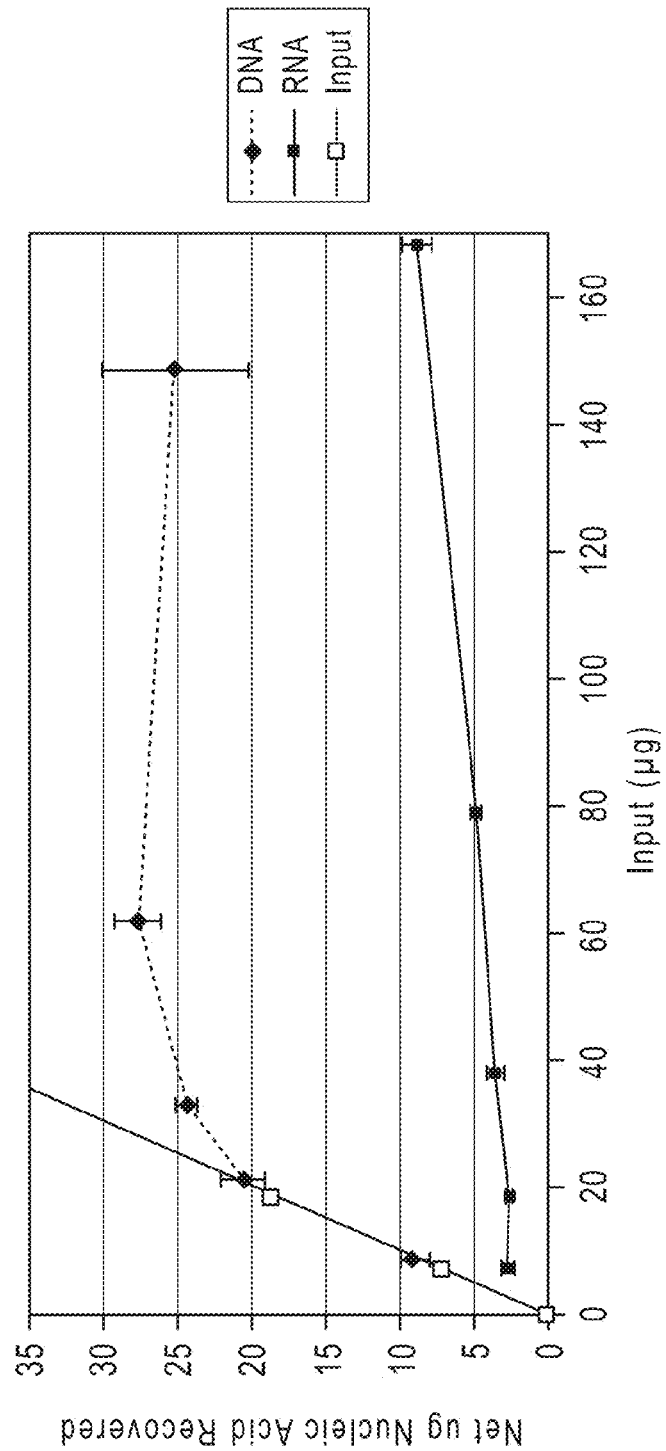
FIG. 10 shows the effect of DNA-selective binding conditions on binding DNA and RNA to Sigma Silica. Increasing concentrations of either DNA or RNA were bound to Sigma Silica using 50 mM Tris, pH 8.0, and 4.8 M NaI.

The results are shown in FIG. 10. Under the binding conditions used in this study, 10 mg of the silicon dioxide particles had a capacity of .about.25 .mu.g for genomic DNA. There was virtually complete recovery of added genomic DNA at concentrations below saturation, indicating that the DNA recovery is efficient. In contrast, RNA recovery was low over the entire range of added RNA. The low amount of RNA recovered may, in fact, have been a result of contaminating RNA in the initial preparation.

Example 10

In order to test whether selectivity resulted from RNA degradation due to the alkalinity of the binding buffer, RNA was incubated either at pH 6 or pH 10 prior to binding to silica under conditions compatible with RNA binding as follows. Total rat liver RNA (25 .mu.g in a total volume of 10 .mu.L) was incubated, in duplicate, in 100 .mu.L of either 50 mM AMP containing pH 10, 4.8 M NaI, or 50 mM MES, pH 6 containing 4.8 M NaI at ambient temperature for 5, 10, 15 30 or 60 minutes. At the end of the indicated time, 1 mL of 50 mM MES, pH 6 containing 4.8 M NaI was added to each tube in order to render conditions compatible with RNA binding to silica. The reactions were mixed and 10 mg of Sigma silicon dioxide (prepared as described in Example 1) in a total volume of 50 .mu.L was added. The samples were incubated at ambient temperature for 10 minutes on a Vortex Genie-2 mixer at setting 7 (Scientific Industries).

Following binding, the particles were centrifuged 14,000 rpm for 1 minute and the supernatant was removed. The particles were subsequently washed twice with 1 ml of 50 mM MES, pH 6 containing 4.8 M NaI followed by four times with 1 mL of 70% ethanol. Following addition of 250 .mu.L of 50 mM Tris, pH 9.0, the particles were incubated for 5-10 minutes at 56.degree. C. with continuous shaking (1400 rpm) on an Eppendorf Thermomixer R. The particles were centrifuged at 14,000 rpm for 1 minute and the supernatant containing eluted nucleic acid was collected. In order to detect the presence of residual bound nucleic acid, 250 .mu.L of 100 mM NaOH was added, the particles were incubated for 5-10 minutes at 56.degree. C. with continuous shaking (1400 rpm) on an Eppendorf Thermomixer R, and the eluted nucleic acid was collected. The amount of nucleic acid in each fraction was quantified spectrophotometrically.

Figure 16:
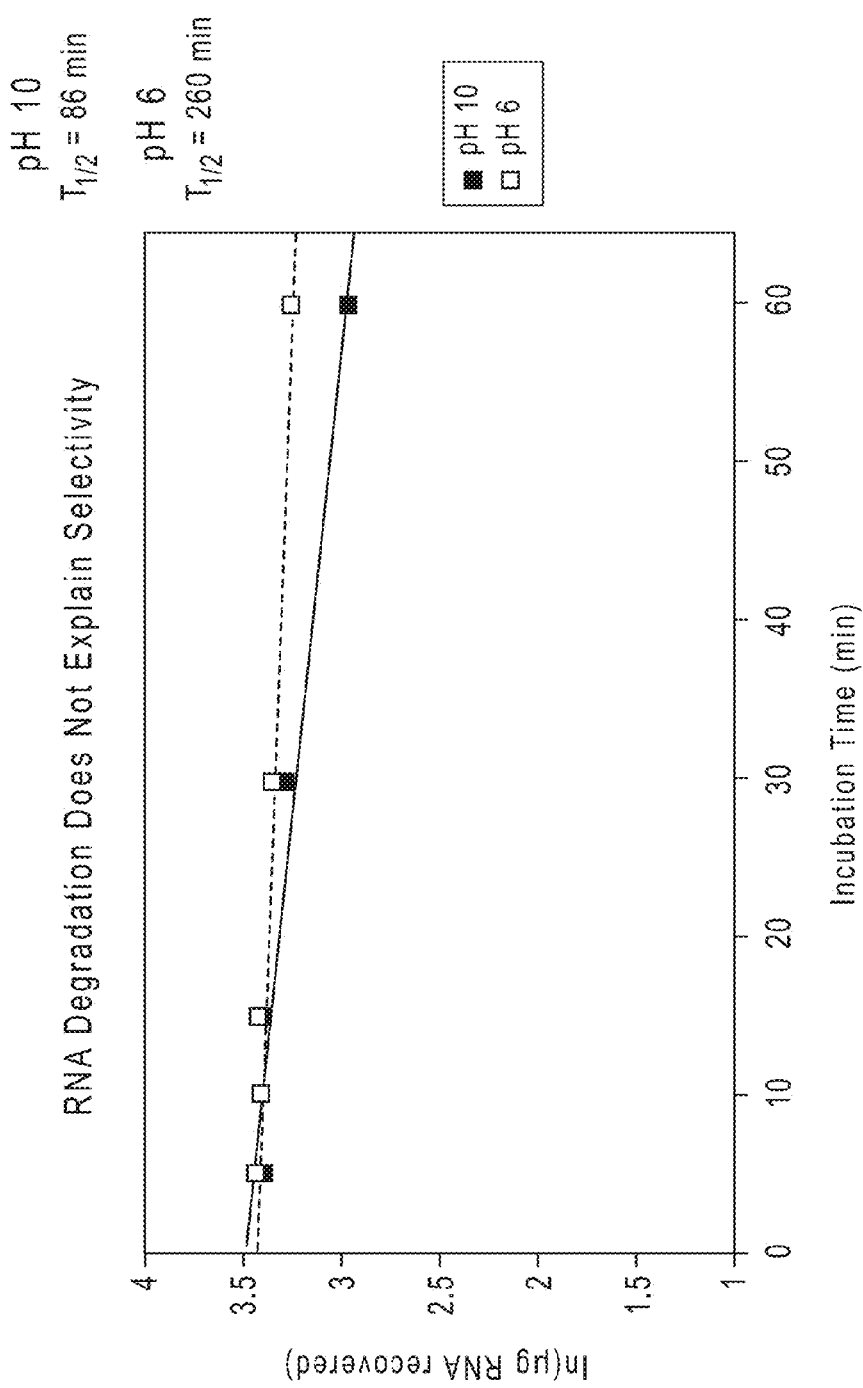
FIG. 16 shows the recovery of RNA after various incubation times in order to test for RNA degradation.

As shown in FIG. 16, the half-life of RNA is 86 minutes and 260 minutes at pH 10 and 6, respectively. Based on these half-lives, only 7.7% and 2.6% of the added RNA would be expected to degrade during a 10 minute binding incubation at pH 10 and 6, respectively.

Example 11

The effect of pH on protein binding was examined. Each condition was assayed once. Purified bovine serum albumin (1 mg, 100 .mu.l of a 10 mg/ml solution in water, New England Biolabs, Lot 938) was added to 1.5 ml microcentrifuge tubes containing 1 ml of: (1) 50 mM MES, pH 6.0, 4.75 M NaI; (2) 50 mM Tris-HCl, pH 8, 4.75 M NaI; or (3) 50 mM AMP, pH 10, 4.75 M NaI. The solid phase (10 mg) was added to the separate buffered protein solutions and the mixtures were incubated at ambient temperature with occasional mixing.

Following the binding incubation, the particles were centrifuged (15,800.times.g, 1 minute), and then washed four times with 0.5 ml of 70% ethanol. Following the last ethanol wash, the particles were allowed to air dry at ambient temperature for 10 minutes. The bound protein was first eluted with 0.25 ml of 50 mM Tris, pH 9 for 5 minutes at 56.degree. C. with constant mixing and the eluted protein was collected. Any residual protein bound to the particles was eluted with 0.25 ml of 0.1 N NaOH at 56.degree. C. for 5 minutes with constant mixing and the eluted protein was collected. The recovery of protein was quantified by spectrophotometry.

Figure 11:
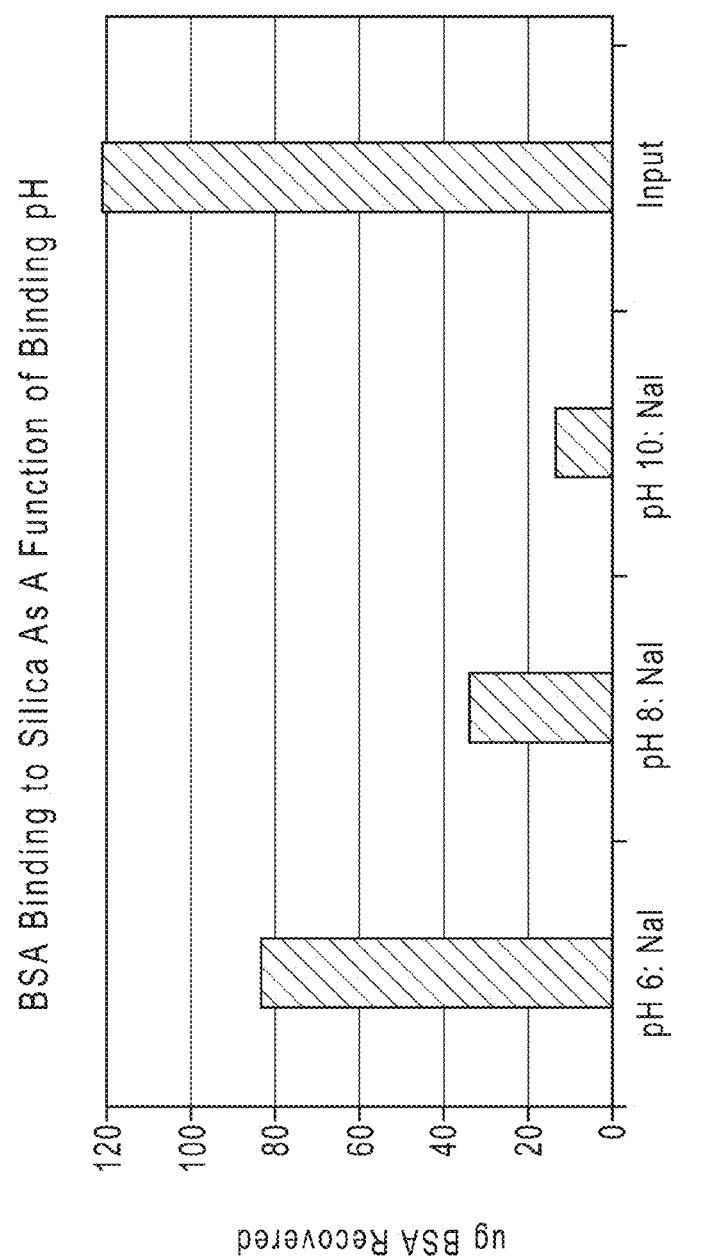
FIG. 11 shows the binding of protein (bovine serum albumin) to silica at various pH levels.
Figure 12A:
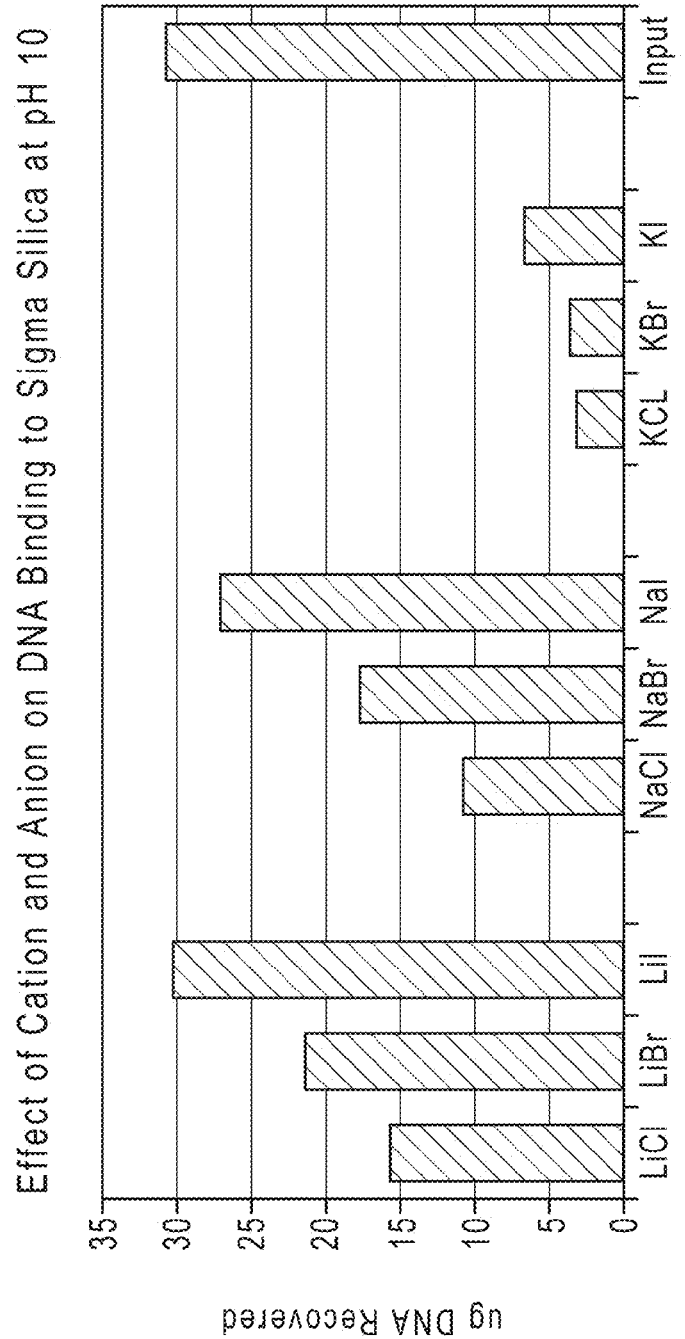
FIG. 12(a) shows the effects of various anions and cations on binding of DNA to Sigma Silica at pH 10 (grouped by cation).
Figure 12B:
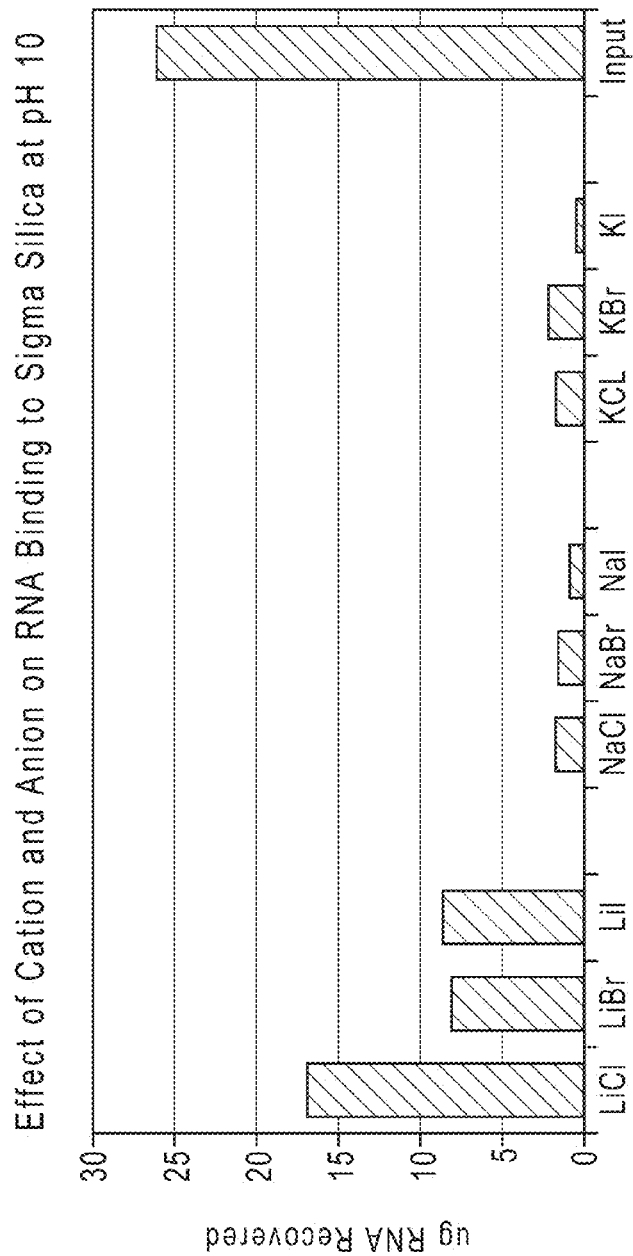
FIG. 12(b) shows the effects of various anions and cations on binding of RNA to Sigma Silica at pH 10 (grouped by cation).
Figure 12C:
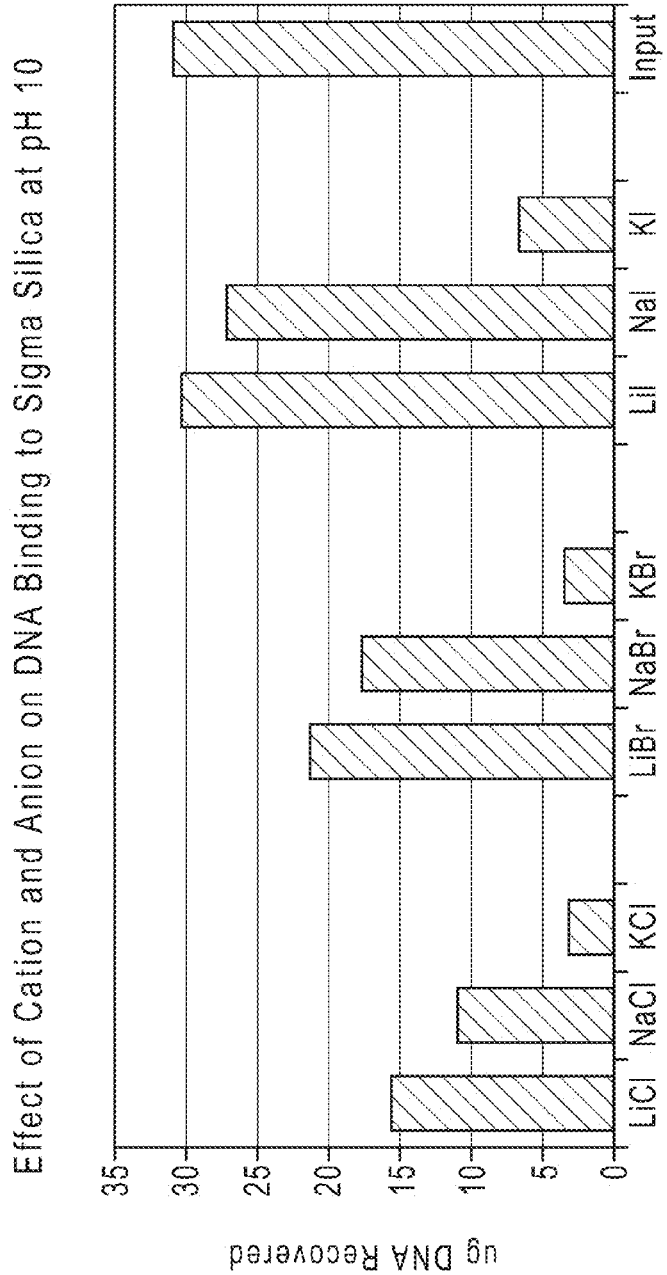
FIG. 12(c) shows the effects of various anions and cations on binding of DNA to Sigma Silica at pH 10 (grouped by anion).
Figure 12D:
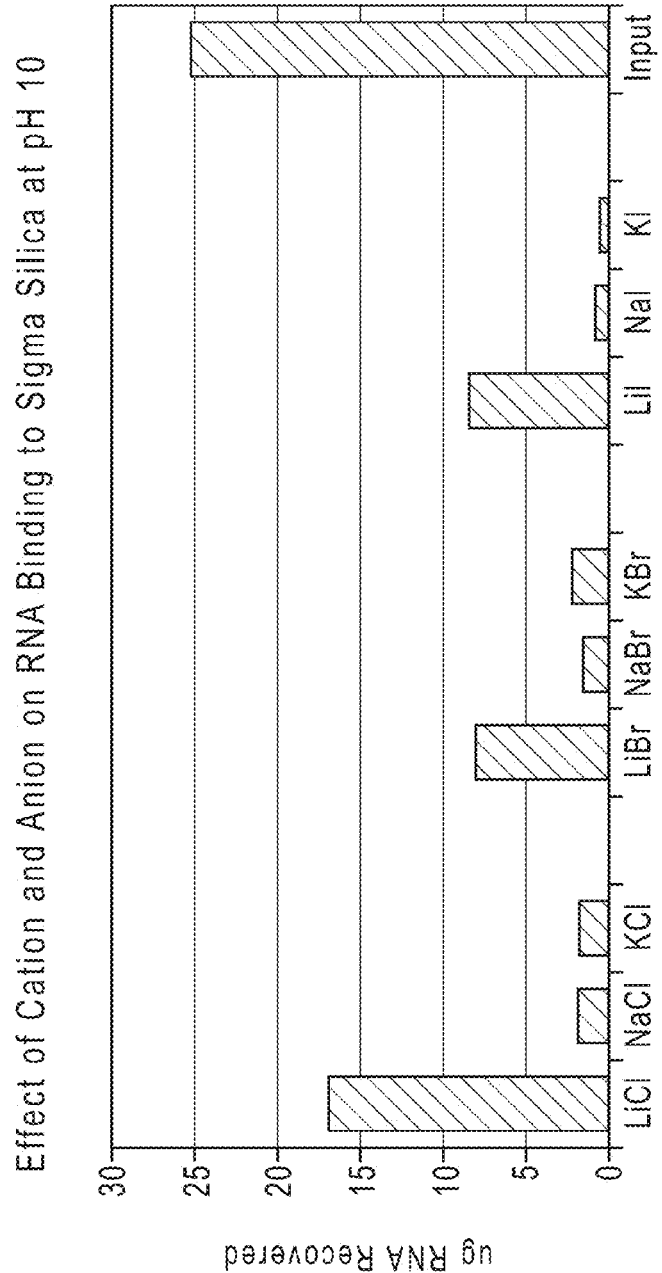
FIG. 12(d) shows the effects of various anions and cations on binding of RNA to Sigma Silica at pH 10 (grouped by anion).
Figure 12E:
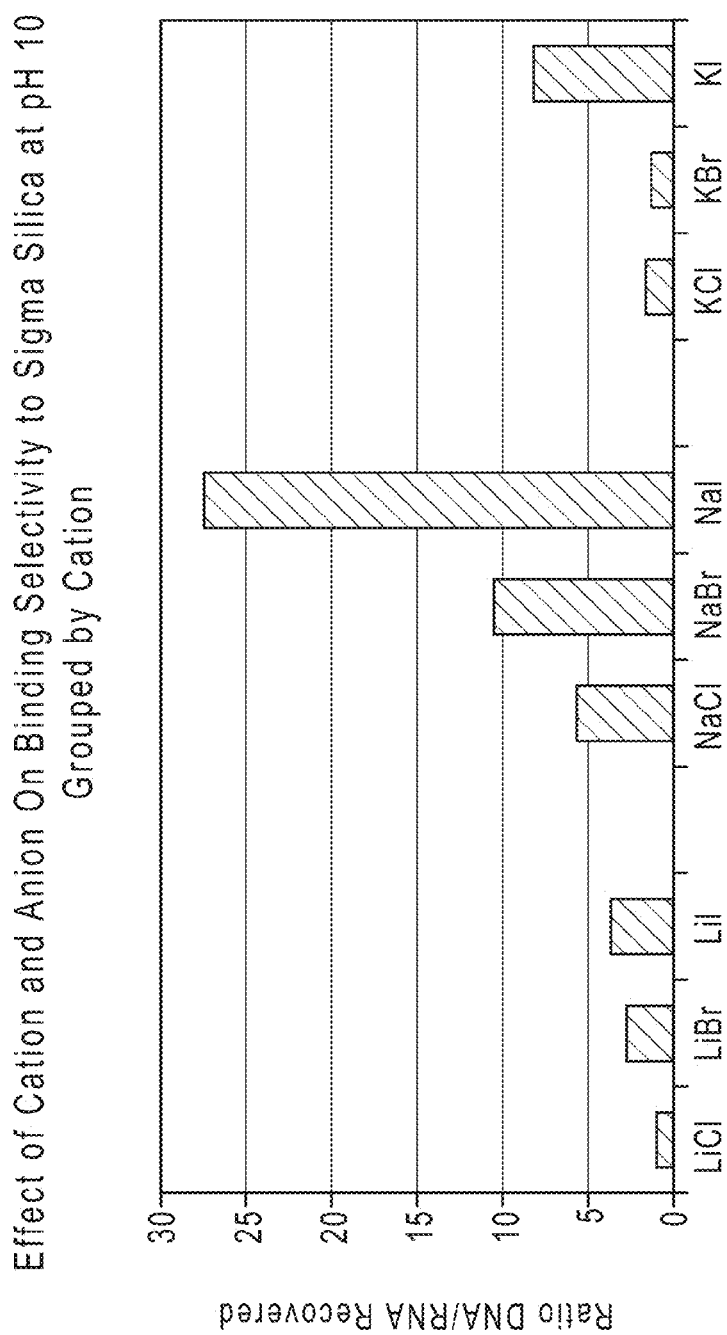
FIG. 12(e) shows the effects of various anions and cations on binding selectivity to Sigma Silica at pH 10 (grouped by cation).
Figure 12F:
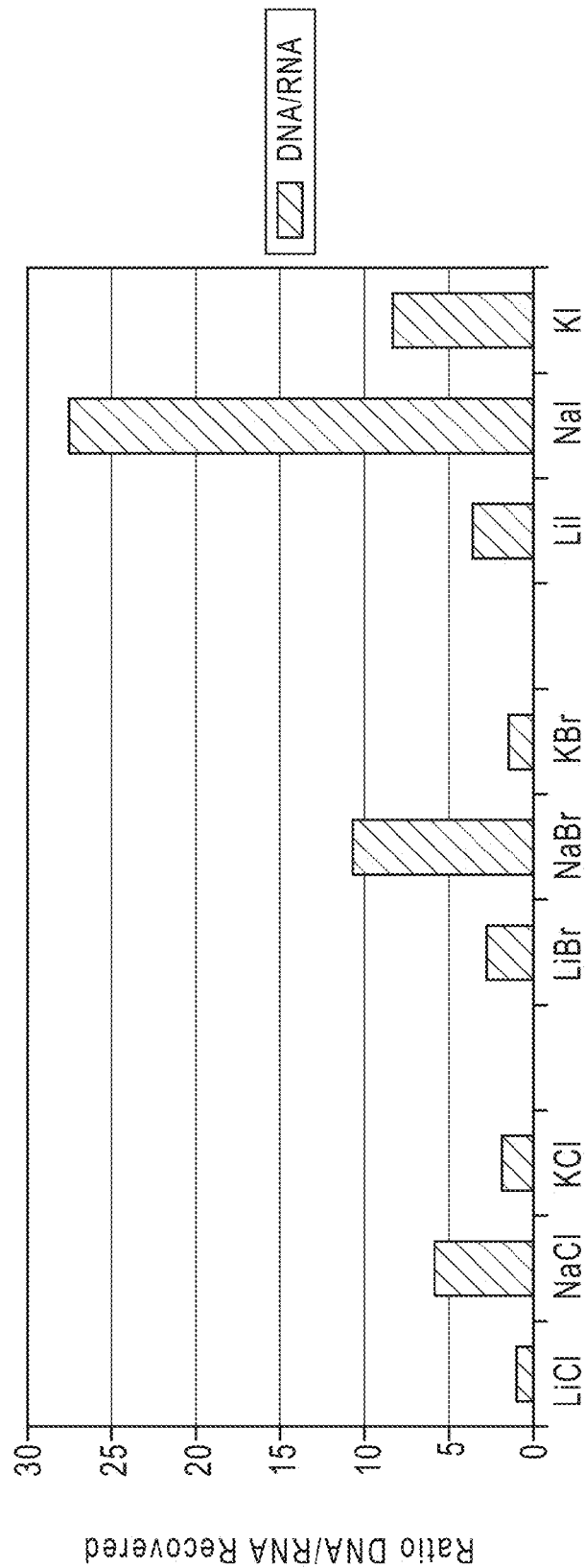
FIG. 12(f) shows the effects of various anions and cations on binding selectivity to Sigma Silica at pH 10 (grouped by anion).

The results are shown in FIG. 11. Like RNA binding, protein binding to silica was reduced as the pH of the binding buffer was increased.

Example 12

The effect of salt composition on DNA and RNA binding to silica was examined at alkaline pH. Silicon dioxide (which is also called Sigma silica) was prepared as described in Example 1. Sheared calf thymus DNA was prepared according to Example 1. Rat liver total RNA was the source of RNA.

Each nucleic acid and buffer combination was assayed once. Either 25 .mu.g (50 .mu.l of a 0.5 mg/ml solution in water) sheared calf thymus DNA or 25 .mu.g (10 .mu.l of a 2.5 mg/ml solution in water) rat liver total RNA was added separately to separate 1.5 ml microcentrifuge tubes containing 0.5 ml of one of the following buffers: (1) 50 mM AMP, pH 10, 3.65 M lithium chloride; (2) 50 mM AMP, pH 10, 3.65 M lithium bromide; (3) 50 mM AMP, pH 10, 3.65 M lithium iodide; (4) 50 mM AMP, pH 10, 3.65 M sodium chloride; (5) 50 mM AMP, pH 10, 3.65 M sodium bromide; (6) 50 mM AMP, pH 10, 3.65 M sodium iodide; (7) 50 mM AMP, pH 10, 3.65 M potassium chloride; (8) 50 mM AMP, pH 10, 3.65 M potassium bromide; or (9) 50 mM AMP, pH 10, 3.65 M potassium iodide.

The solid phase (10 mg) was added to each of the 18 buffered nucleic acid solutions and the mixtures were incubated for 10 minutes at ambient temperature with occasional mixing. Following the binding incubation, the particles were centrifuged (15,800.times.g, 1 minute) and washed four times with 0.5 ml of 70% ethanol. The bound nucleic acid was first eluted with 0.25 ml of 10 mM Tris, pH 9, for 5 minutes at 56.degree. C. with constant mixing and the eluted nucleic acid was collected. Any residual nucleic acid bound to the particles was eluted with 0.25 ml of 0.1 N NaOH at 56.degree. C. for 5 minutes with constant mixing and the eluted nucleic acid was collected. The recovery of nucleic acid was quantified by spectrophotometry.

The results are shown in FIGS. 12(a)-(f). To facilitate analysis, the data is shown grouped by cation or anion.

At pH 10, binding of DNA was influenced by the composition of the anion. DNA binding to silicon dioxide (Sigma silica) increased as the monovalent anion radius was increased. The radius of the monovalent cation influenced the magnitude of that effect. In contrast, the binding of RNA to silica showed a tendency to decrease as the anion radius was increased. Decreasing the size of the cation increased the capacity of the silicon dioxide for both nucleic acid species. As a result, selectivity for DNA binding could be improved with certain selections of salt composition. These results showed that the larger the anion, the greater the selectivity. There was no correlation between the cation radius and selectivity. Sodium demonstrated the highest degree of selectivity for DNA binding.

Example 13

To demonstrate discrimination of the selective conditions for isolating DNA, the ability of high concentrations of RNA to inhibit binding of genomic DNA was examined. Silicon dioxide and genomic DNA was prepared as described in Example 1. Rat liver total RNA was the source of RNA.

Each condition was assayed once. Five separate 10 .mu.l mixtures of RNA and DNA at RNA:DNA ratios of 1:1 (15 .mu.g:15 .mu.g), 10:1 (15 .mu.g:1 .mu.g), 30:1 (15 .mu.g:0.5 .mu.g), or 100:1 (20 .mu.g:0.2 .mu.g), were added to separate 1.5 ml microcentrifuge tubes containing 0.45 ml of one of the following buffers: (1) 50 mM AMP, pH 10, 4.75 M NaI; or (2) 50 mM MES, pH 6.0, 4.75 M NaI. The solid phase (10 mg) was added to each of the 10 buffered nucleic acid solution combinations and the mixtures were incubated for 10 minutes at ambient temperature with occasional mixing.

Following the binding incubation, the particles were centrifuged (15,800.times.g, 1 minute) and washed four times with 0.5 ml of 70% ethanol. Following the last ethanol wash, the particles were washed once with 0.5 ml of acetone. Once the acetone was removed, the pellets were dried for 5 minutes at 56.degree. C. The bound nucleic acid was eluted with 50 .mu.l of 10 mM Tris, pH 9, for 5 minutes at 56.degree. C. with constant mixing and the eluted nucleic acid was collected.

Figure 13:
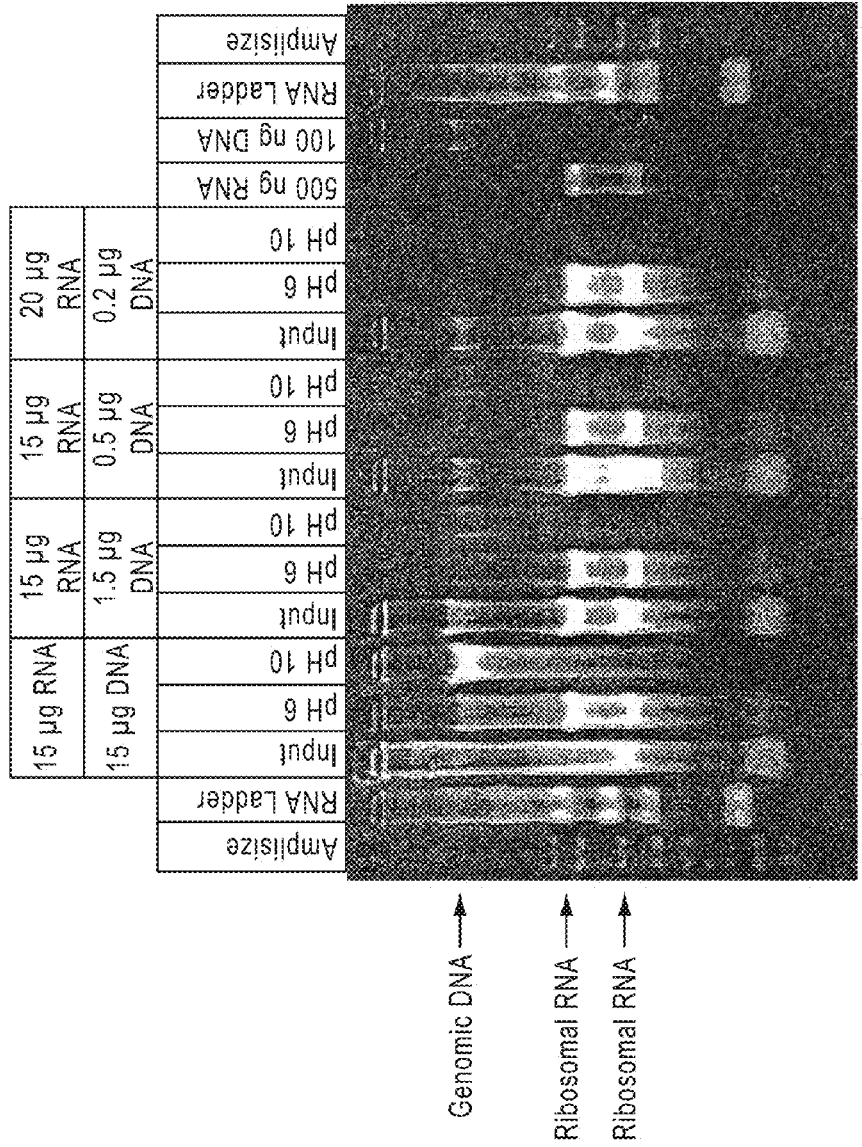
FIG. 13 shows the results of selective binding experiments with various concentrations of DNA at pH 6 or pH 10.

The recovery of nucleic acid was visualized by agarose gel electrophoresis (see FIG. 13). Electrophoresis was performed on 2 .mu.l of the nucleic acid stock mixes or 5 .mu.l of the isolated eluate. Samples were electrophoresed through a 1% SeaKem® (Teknova), 0.5 .mu.g/ml ethidium bromide gel using 1.times.TBE, 0.5 .mu.g/ml ethidium bromide buffer (BIO-RAD), at 8V/cm for 30 minutes to 1 hour. Ethidium-stained material was visualized and photographed under short wave ultra-violet light. Molecular weight markers consisted of an AmpliSize DNA molecular weight standard (BIO-RAD) and an RNA ladder (GIBCO BRL).

At pH 10 in NaI, silica was at least 40-fold more selective for DNA than RNA. At pH 6, there was nearly complete capture of the added RNA. At the highest level of added RNA (20 .mu.g), no detectable RNA was recovered at pH 10. In contrast, when 0.5 .mu.g of genomic DNA was added, detectable DNA was recovered. Therefore, at pH 10, in the presence of sodium iodide, silica showed greater that 40-fold greater selectivity for DNA than RNA.

Example 14

To evaluate whether high levels of RNA would compete with DNA for binding to a solid phase, high levels of RNA were mixed with genomic DNA and bound under both non-selective and selective conditions. Sigma silicon dioxide and sheared genomic DNA was prepared as described in Example 1. Rat liver total RNA (Biochain Institute, lot numbers A304057, A305062, or A306073) was the source of RNA.

Each nucleic acid and buffer combination was assayed twice. Either (a) 5 .mu.g sheared calf thymus DNA (10 .mu.l of 0.5 mg/ml) and 5 .mu.g (2 .mu.l of 2.5 mg/ml) of rat liver total RNA, or (b) 5 .mu.g sheared calf thymus DNA (10.mu.l of 0.5 mg/ml) and 50 .mu.g (20 .mu.l of 2.5 mg/ml) of rat liver total RNA was added separately and mixed in separate 1.5 ml microcentrifuge tubes containing 0.45 ml of one of the following buffers: (1) 50 mM AMP, pH 10, 3.5 M NaI; or (2) 50 mM MES, pH 6.0, 3.5 M NaI. The solutions were incubated at ambient temperature for 5 minutes.

The solid phase (10 mg) was added to each of the four buffered nucleic acid solution combinations and the mixtures were incubated for 10 minutes at ambient temperature with occasional mixing. Following the binding incubation, the particles were centrifuged (15,800.times.g, 1 minute), and washed three times with 0.5 ml of 70% ethanol. The bound nucleic acid was eluted with 100 .mu.l of 10 mM Tris, pH 9 for 5 minutes at 56.degree. C. with constant mixing and the eluted nucleic acid was collected.

Figure 14:
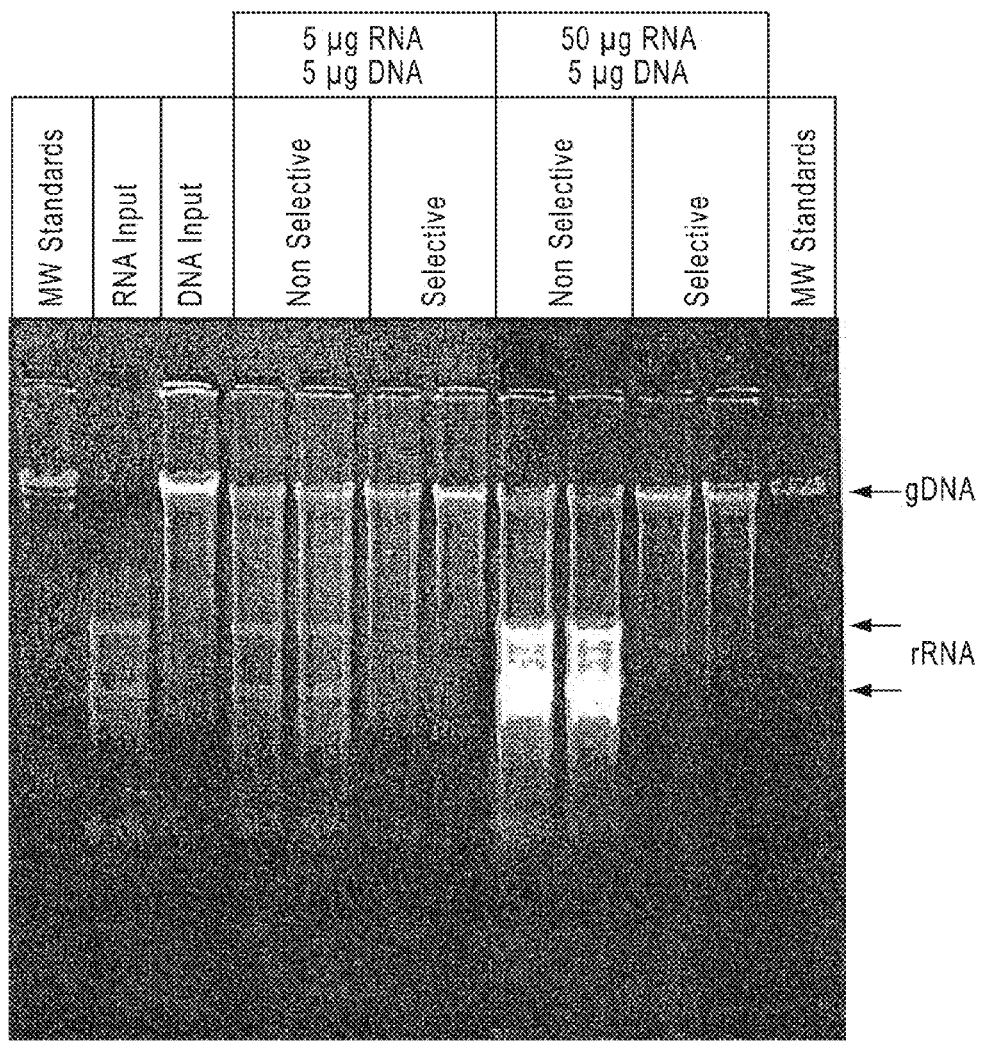
FIG. 14 shows the results of DNA and RNA recovery under selective and nonselective conditions with different ratios of RNA to DNA.

The recovery of nucleic acid was visualized by agarose gel electrophoresis (see FIG. 14). Of the isolation eluate, 10 .mu.l was electrophoresed through a 0.8% SeaKem agarose gel as described in Example 13. Ethidium-stained material was visualized and photographed under a short wave ultra-violet light.

Even at excess RNA concentrations, little RNA was isolated under the DNA selective conditions. The data showed that the amount of RNA contamination was lower than the limit of detection when using selective conditions. Under nonselective conditions, at high concentrations of nucleic acids, the limited number of nucleic acid binding sites may reduce overall DNA recovery.

Example 15

Genomic DNA was isolated from whole human blood as follows. Silicon dioxide was prepared as described in Example 1.

Each condition was assayed once. Either 25 .mu.l or 100 .mu.l of whole blood (Blood Centers of the Pacific) was added separately to separate 1.5 ml microcentrifuge tubes containing either 0.25 ml or 0.9 ml (respectively) of one of the following buffers: (1) 50 mM MES, pH 6.0, 4.75 M NaI, or (2) 50 mM AMP, pH 10, 4.75 M NaI. Nucleic acid was incubated 10 minutes at ambient temperature in the buffered solution, with occasional mixing.

The solid phase (10 mg) was added to the four buffered nucleic acid solution combinations, and the mixtures were incubated 10 minutes at ambient temperature with occasional mixing. Following the binding incubation, the particles were centrifuged (15,800.times.g, 1 minute), and washed twice with 0.5 ml of the binding buffer that had been used for the binding incubation. Subsequently, the particles were washed four times with 70% ethanol. The bound nucleic acid was eluted with 50 .mu.l of 10 mM Tris, pH 9 for 5 minutes at 56.degree. C. with constant mixing and the eluted nucleic acid was collected.

Figure 15:
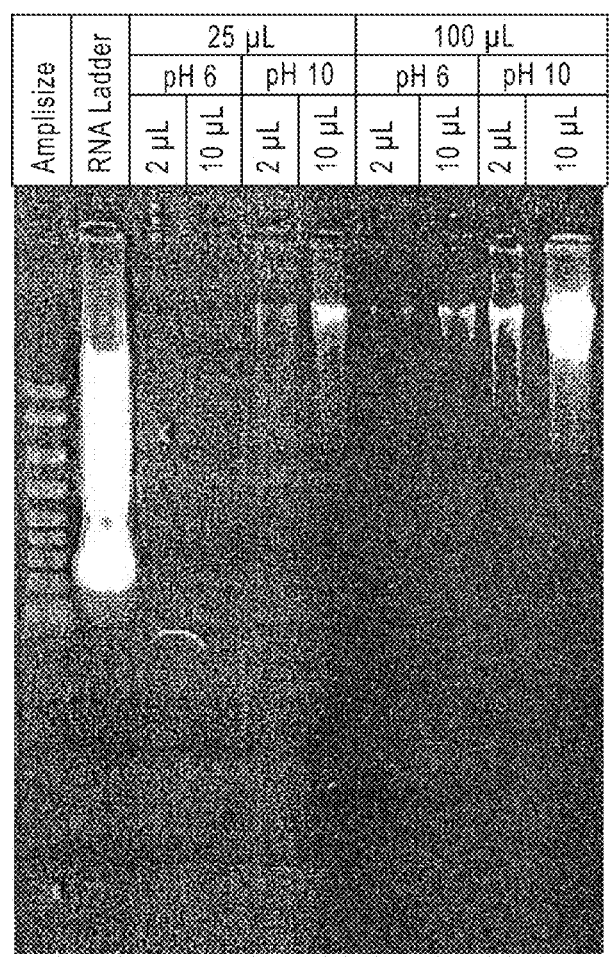
FIG. 15 shows the results of extraction of DNA from whole blood using Sigma Silica at pH 6 and pH 10.

The recovery of nucleic acid was visualized by agarose gel electrophoresis (see FIG. 15). Either 2 .mu.l or 10 .mu.l of the isolation eluate was electrophoresed through 1.0% SeaKem agarose gel as described in Example 13. Ethidium-stained material was visualized and photographed under short wave ultra-violet light.

When silica was added to whole blood in NaI-containing buffer at pH 6, the particles clump, suggesting that protein also adsorbed to the particles. As a result, DNA recovery was poor. In contrast, the silica particles remained in suspension when added to blood at pH 10. In the absence of protein adsorption to the particles, DNA recovery was high.

Example 16

Figure 17:
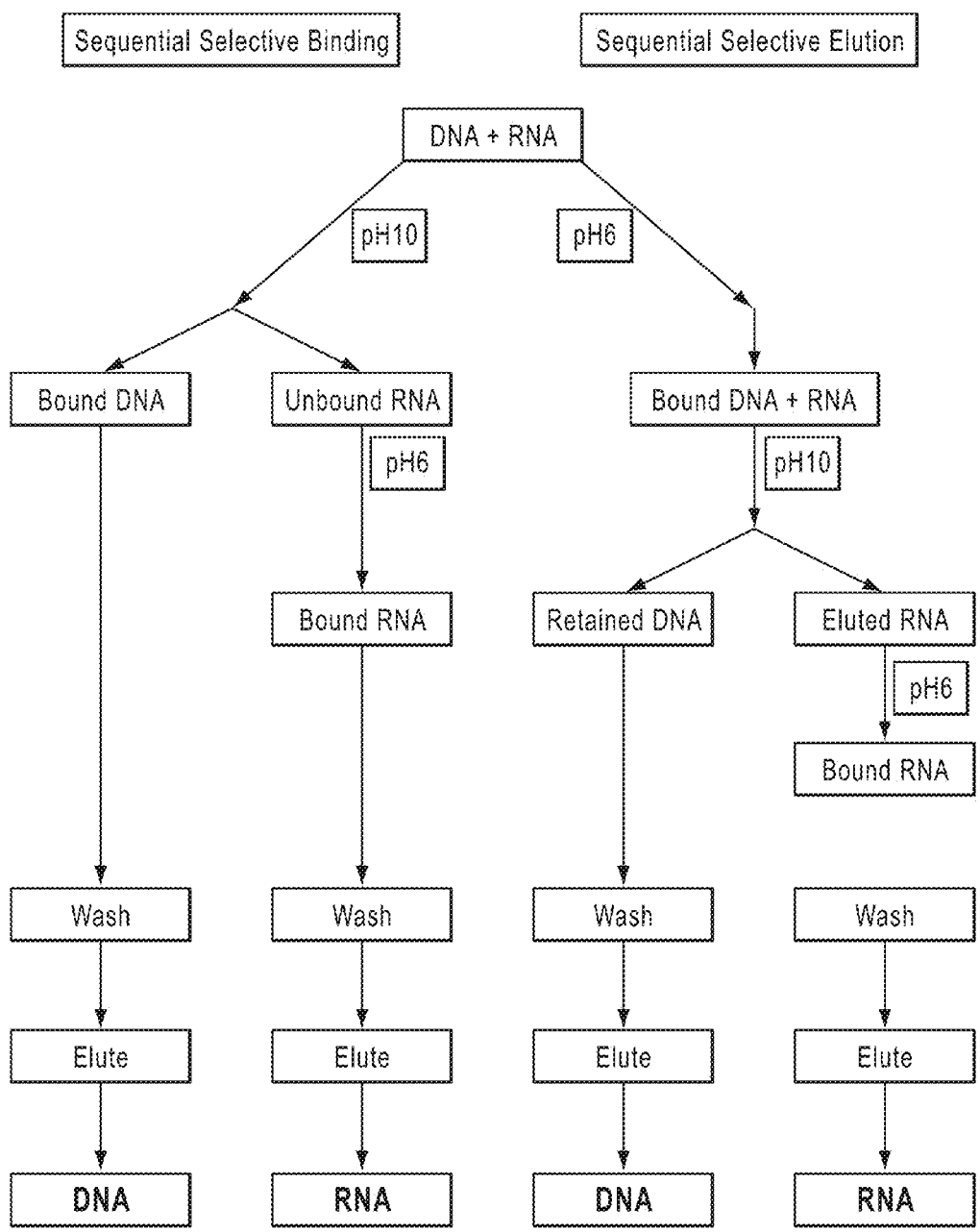
FIG. 17 shows a schematic diagram of certain methods of isolating nucleic acids by selective binding and elution.

In certain embodiments, both DNA and RNA can be isolated from a sample mixture by sequential selective binding (sequential selective binding). An exemplary sequential selective binding is shown in FIG. 17. In sequential selective binding, the sample is contacted with the solid phase under conditions compatible with selective DNA binding. The solid phase containing the bound DNA is separated from the unbound material, and the conditions in the unbound fraction are adjusted to those compatible with RNA binding to the solid phase. A second solid phase is added to this second fraction to adsorb the RNA. DNA and RNA are then isolated from the respective solid phases.

To evaluate an embodiment of sequential selective binding of DNA and RNA, a mixture of the two was processed under sequential selective binding conditions. First, the DNA was bound to the solid phase under DNA selective conditions and then the unbound RNA fraction was removed and bound to the same solid phase using nonselective binding conditions. Sigma silicon dioxide and sheared genomic DNA was prepared as described in Example 1. Rat liver total RNA (Biochain Institute) was the source of RNA.

Each nucleic acid and buffer combination was assayed twice. 5 pg DNA, 5 .mu.g RNA and a mixture of 5 .mu.g DNA and 5 .mu.g RNA were added to separate 1.5 ml microcentrifuge tubes containing 50 mM AMP, pH 10, 3.5 M NaI; 50 mM MES, pH 6, 3.5 M NaI; and 50 mM AMP, pH 10, 3.5 M NaI respectively. The buffered solutions were incubated for 5 minutes at ambient temperature. 10 mg of the solid phase was added to each of the 6 buffered nucleic acid solution combinations and the mixtures were incubated for 10 minutes at ambient temperature with occasional mixing.

Following the binding incubation, the particles were centrifuged (15,800.times.g, 1 minute) and washed 3 times with 0.5 ml of 70% ethanol. Once the ethanol was removed, the particles were allowed to dry at ambient temperature at least 10 minutes.

The supernatants from the binding reactions of the mixture of DNA and RNA were taken and added to separate 1.5 ml microcentrifuge tubes containing 1 mL of 50 mM MES, pH 6, 3.5 M NaI. To these tubes was added 10 mg of the solid phase and the mixtures were incubated for 10 minutes at ambient temperature with occasional mixing.

Following the binding incubation, the particles were centrifuged (15,800.times.g, 1 minute) and washed 3 times with 0.5 mL of 70% ethanol. Once the ethanol was removed, the particles were allowed to dry at ambient temperature at least 10 minutes.

The bound nucleic acid was eluted from all particles with 0.1 mL of 10 mM Tris-HCl, pH 9, for 5 minutes at 56.degree. C. wiith constant mixing and the eluted nucleic acid collected.

Figure 18:
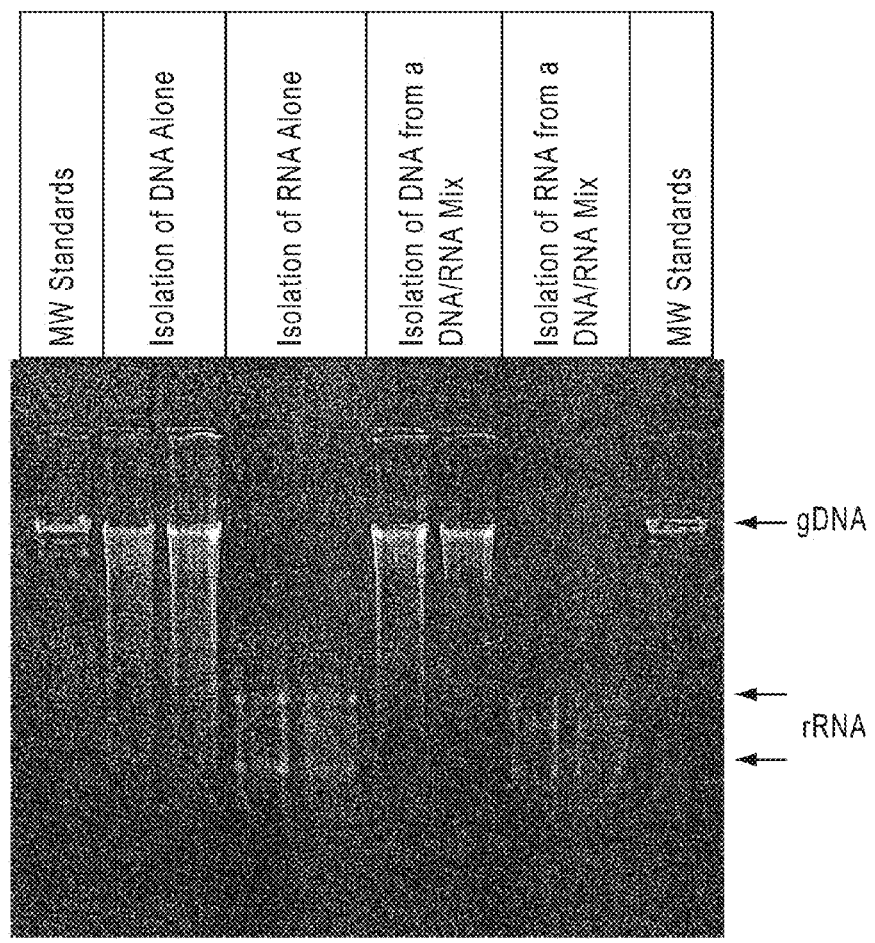
FIG. 18 shows a stained agarose gel showing RNA and DNA isolated by an exemplary sequential selective binding method.

The recovery of nucleic acid was visualized by agarose gel electrophoresis. Electrophoresis was performed on 10 .mu.L of the isolated eluate. Samples were electrophoresed through a 0.8% SeaKem™, 0.5.mu.g/mL ethidium bromide gel using 1.times.TBE, 0.5 .mu.g/mL ethidium bromide buffer (BIO-RAD), at 7V/cm for 30 minutes to 1 hour. Ethidium-stained material was visualized and photographed under short wave ultra-violet light. Molecular weight markers consisted of High Molecular Weight DNA Markers (GIBCO BRL). The results are shown in FIG. 18.

Example 17

In certain embodiments, both DNA and RNA can be isolated from a sample mixture by first binding both species to a solid phase and sequentially releasing each nucleic acid type under the appropriate conditions (sequential specific elution). An exemplary sequential selective elution is shown in FIG. 17. In sequential selective elution, the sample is contacted with the solid phase under conditions that bind both DNA and RNA. Following washes, the RNA is released under conditions that bind only DNA. The solid phase is removed and the DNA and RNA are subsequently purified from both fractions.

To evaluate an embodiment of sequential selective elution, mixtures of DNA and RNA were contacted with the solid phase under conditions which would bind both. The RNA is eluted under conditions which bind only DNA, and the DNA is subsequently eluted using a low ionic strength buffer. Sigma silicon dioxide and sheared genomic DNA was prepared as described in Example 1. Rat liver total RNA (Biochain Institute) was the source of RNA.

Each nucleic acid and buffer combination was assayed twice, and the DNA and RNA was processed as follows. Either (1) 10 .mu.g sheared calf thymus DNA, or (2) 10 .mu.g rat liver total RNA, or (3) 10 .mu.g sheared calf thymus DNA and 10 .mu.g rat liver total RNA was added to separate 1.5 ml microcentrifuge tubes containing 0.2 ml 50 mM MES, pH 6, 3.5 M sodium iodide, and incubated five minutes at ambient temperature with occassional mixing. The solid phase (10 mg) was added to each of the buffered nucleic acid solutions and the mixtures were incubated for 10 minutes at ambient temperature with mixing.

Following the binding incubation, the particles—with the exception of one replicate set of particles with both DNA and RNA bound—were centrifuged (15,800.times.g, 1 minute) and the bound nucleic acid was eluted with 0.2 mL 10 mM Tris, pH 9 for 5 minutes at 56.degree. C. with constant mixing, and the eluted nucleic acid was collected.

One replicate set of particles with both DNA and RNA bound were washed with 0.2 ml 50 mM AMP, pH 10, 3.5 M NaI, for 5 minutes at ambient temperature with occasional mixing, and the RNA was eluted and collected. The particles were then washed with 0.2 ml 10 mM Tris, pH 9 for 5 minutes at 56.degree. C. with constant mixing, and the bound DNA was eluted and collected.

Figure 19:
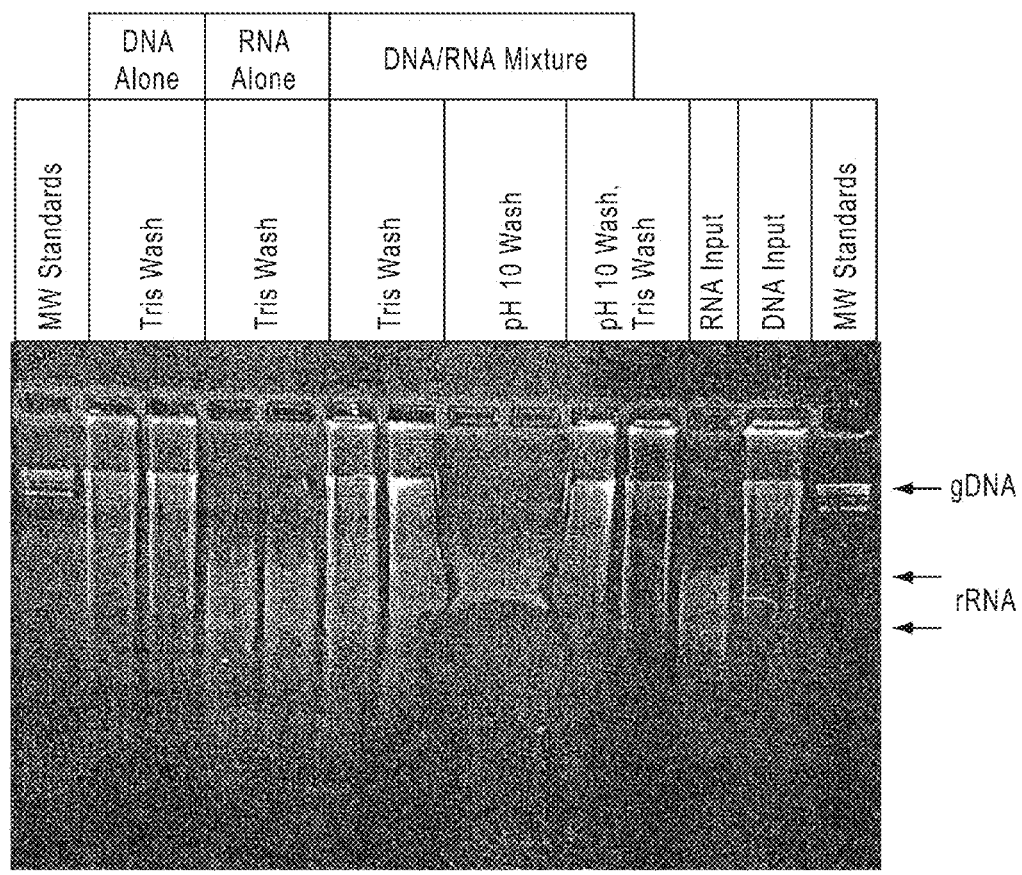
FIG. 19 shows a stained agarose gel showing RNA and DNA isolated by an exemplary sequential selective elution method.

The recovery of nucleic acid was visualized by agarose gel electrophoresis. Of the isolation eluate, 10 .mu.L was electrophoresed through a 1% SeaKem®, 0.5 .mu.g/mL ethidium bromide gel using 1.times.TBE, 0.5.mu.g/mL ethidium bromide buffer (BIO-RAD), at 7V/cm for 30 minutes to 1 hour. Ethidium-stained material was visualized and photographed under short wave ultra-violet light. Molecular weight markers consisted of High Molecular Weight DNA Markers (GIBCO BRL). The results are shown in FIG. 19.

The invention claimed is:

1. A method for identifying DNA and RNA in a biological sample comprising:
   selectively binding DNA to a first solid phase by contacting the biological sample with the first solid phase under conditions which selectively bind DNA;
   separating the first solid phase with the bound DNA from a first unbound portion of the biological sample;
   identifying the DNA bound to the first solid phase; and
   identifying the RNA from the first unbound portion of the biological sample.

2. The method of claim 1, wherein the identifying the DNA bound to the first solid phase comprises amplifying the DNA bound to the first solid phase.

3. The method of claim 1, wherein the conditions which selectively bind DNA comprise using a binding buffer comprising picrate, tannate, tungstate, molybdate, perchlorate, sulfosalicylate, trichloroacetate, tribromoacetate, thiocyanate, nitrate, iodide or bromide.

4. The method of claim 1, wherein the conditions which selectively bind DNA comprise using a binding buffer comprising trichloroacetate, tribromoacetate, thiocyanate, or nitrate.

5. The method of claim 1, wherein the conditions which selectively bind DNA comprise using a binding buffer comprising thiocyanate, iodide or bromide.

6. The method of claim 1, wherein the conditions which selectively bind DNA comprise using a binding buffer comprising thiocyanate.

7. The method of claim 1, wherein the DNA is genomic DNA.

8. The method of claim 1, wherein the DNA is genomic DNA and the conditions which selectively bind genomic DNA comprise using a binding buffer comprising thiocyanate, or iodide.

9. The method of claim 1, wherein the DNA is genomic DNA and the conditions which selectively bind genomic DNA comprise using a binding buffer comprising thiocyanate.

10. The method of claim 7, wherein identifying the genomic DNA bound to the first solid phase comprises hybridization to labeled probes, mass spectrometry, or detection by a reaction of the bound DNA with a label.

11. The method of claim 10 wherein detection by a reaction of the bound genomic DNA with a label comprises detection of fluorescence following the addition of a DNA-binding fluorophore.

12. The method of claim 7, wherein identifying the genomic DNA bound to the first solid phase comprises hybridization to labeled probes.

13. The method of claim 1, wherein the solid phase is in a form selected from a group comprising a particle, a bead, a membrane, and a frit.

* * * * *